US009078903B2

(12) United States Patent
Laurent-Applegate et al.

(10) Patent No.: US 9,078,903 B2
(45) Date of Patent: *Jul. 14, 2015

(54) COMPOSITIONS FOR THE TREATMENT OF SKIN CONDITIONS, DISORDERS OR DISEASES AND METHODS OF MAKING AND USING THE SAME

(71) Applicant: Merz GmbH & Co. KGaA, Allschwil (CH)

(72) Inventors: Lee Laurent-Applegate, Bercher (CH); Patrick Hohlfeld, Lausanne (CH)

(73) Assignee: MERZ GMBH & CO. KGAA, Allschwil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/741,657

(22) Filed: Jan. 15, 2013

(65) Prior Publication Data

US 2013/0129691 A1 May 23, 2013

Related U.S. Application Data

(63) Continuation of application No. 10/361,450, filed on Feb. 10, 2003, now Pat. No. 8,394,371.

(60) Provisional application No. 60/356,034, filed on Feb. 11, 2002.

(51) Int. Cl.
| | |
|---|---|
| *A01N 63/00* | (2006.01) |
| *A61K 35/54* | (2015.01) |
| *A61K 35/36* | (2015.01) |
| *A61L 27/24* | (2006.01) |
| *A61L 27/38* | (2006.01) |
| *A61L 27/60* | (2006.01) |
| *C12N 5/077* | (2010.01) |
| *A61K 35/12* | (2015.01) |

(52) U.S. Cl.
CPC ............ *A61K 35/54* (2013.01); *A61K 35/36* (2013.01); *A61L 27/24* (2013.01); *A61L 27/3804* (2013.01); *A61L 27/3813* (2013.01); *A61L 27/3834* (2013.01); *A61L 27/3895* (2013.01); *A61L 27/60* (2013.01); *C12N 5/0652* (2013.01); *C12N 5/0656* (2013.01); *A61K 35/12* (2013.01)

(58) Field of Classification Search
CPC ....... A61K 35/12; A61K 35/36; A61K 35/54; A61L 27/24; A61L 27/3804; A61L 27/3813
See application file for complete search history.

(56) References Cited

U.S. PATENT DOCUMENTS

| | | | |
|---|---|---|---|
| 4,418,691 A | 12/1983 | Yannas et al. | |
| 4,458,678 A | 7/1984 | Yannas et al. | |
| 5,015,584 A | 5/1991 | Brysk | |
| 5,068,315 A | 11/1991 | Buultjens et al. | |
| 5,460,939 A | 10/1995 | Hansbrough et al. | |
| 5,489,304 A | 2/1996 | Orgill et al. | |
| 5,512,475 A | 4/1996 | Naughton et al. | |
| 5,541,107 A | 7/1996 | Naughton et al. | |
| 5,798,334 A | 8/1998 | Cutroneo | |
| 5,866,167 A | 2/1999 | Van Bossuyt | |
| 5,976,878 A | 11/1999 | Boyce | |
| 6,039,760 A | 3/2000 | Eisenberg | |
| 6,110,208 A | 8/2000 | Soranzo et al. | |
| 6,179,872 B1 | 1/2001 | Bell et al. | |
| 6,270,781 B1 | 8/2001 | Gehlsen | |
| 2002/0068051 A1 | 6/2002 | Dai et al. | |
| 2006/0058238 A1 | 3/2006 | Laurent-Applegate et al. | |

FOREIGN PATENT DOCUMENTS

| | | |
|---|---|---|
| JP | 6316530 A | 11/1994 |
| WO | WO-9624661 A1 | 8/1996 |
| WO | WO-9836704 A1 | 8/1998 |
| WO | WO-9840027 A1 | 9/1998 |
| WO | WO-9943270 A1 | 9/1999 |
| WO | WO 9949878 A1 * | 10/1999 |
| WO | WO-0076437 A1 | 12/2000 |
| WO | WO-0132129 A2 | 5/2001 |
| WO | WO-2004053101 A2 | 6/2004 |
| WO | WO-2006092668 A2 | 9/2006 |

OTHER PUBLICATIONS

French M.M. et al., Chondrogenic Differentiation of Adult Dermal Fibroblasts, Annals of Biomedical Engineering, 2004, vol. 32, No. 1, pp. 50-56.*
Watson D. Various treatments of facial wrinkles, American Academy of Facial and Reconstructive Plastic Surgery; Published Dec. 29, 2001 on the web at—http://www.deborahwatsonmd.com/procedures/procedure-facial.html, pp. 1-3.*
"Average Animal Gestation Periods and Incubation Times." *MSN Encarta-Multimedia.* Web. Dec. 7, 2005.
"Prevent." Merriam-Webster OnLine. Web. Dec. 8, 2005.
Bianchini et al. "Immunological Safety Evaluation of a Horse Collagen Haemostatic Pad." *ArzneimForschDrugRes.* 51.1(2001):414-419.
Cass et al. "Scar Wars: Implications of Fetal Wound Healing for the Pediatric Burn Patient." *Pediatr. Surg. Int.* 12(1997):484-489.
Chin et al. "Differential Expression of Receptor Tyrosine Kinase and Shc in Fetal and Adult Rat Fibroblasts: Toward Defining Scarless Versus Scarring Fibroblast Phenotypes." *Plast. Reconstruct. Surg.* 105.3(2000):972-979.
Dale et al. "Expression of Epidermal Keratins and Filaggrin During Human Fetal Skin Development." *J. Cell Biol.* 101(1985):1257-1269.
Ennis et al. "Leg Ulcers: A Practical Approach to the Leg Ulcer Patient." *Ostomy/Wound Manage.* 41.7ASupplement(1995):52S-62S.
Erdag et al. "Cryopreservation of Fetal Skin is Improved by Extracellular Trehalose." *Cryobiol.* 44.3(2002):218-228.

(Continued)

*Primary Examiner* — Satyendra Singh
(74) *Attorney, Agent, or Firm* — Mintz Levin Cohn Ferris Glovsky and Popeo, P.C.; Terri Shieh-Newton

(57) ABSTRACT

The present invention includes methods and compositions designed for treating a subject suffering from a skin condition, disorder or disease. The compositions include undifferentiated fetal skin cells that are either integrated with a collagen matrix or a carrier.

19 Claims, 12 Drawing Sheets

(56) References Cited

OTHER PUBLICATIONS

Fauza et al. "Videofetoscopically Assisted Fetal Tissue Engineering: Skin Replacement." *J. Pediatric Surg.* 33.2(1998):357-361.

Hirai et al. "Epimorphin: A Mesenchymal Protein Essential for Epithelial Morphogenesis." *Cell.* 69.3(1992):471-481.

Hohlfeld et al. "Tissue Engineered Fetal Skin Constructs for Paediatric Burns." *Lancet.* 366.9488(2005):840-842.

Kolokol'tsova et al. "Prospects of Certified Human Fetal Fibroblasts in the Treatment of Wounds of Various Etiology." *Vestnik Rossiiskoi Akademii Meditsinskikh Nauk.* 3(1998):32-35. (English Abstract Only).

Lorenz et al. "Scarless Wound Repair: A Human Fetal Skin Mold." *Development.* 114(1992):253-259.

Lorenz et al. "The Fetal Fibroblast: The Effector Cell of Scarless Fetal Skin Repair." *Plast. Reconstruct. Surg.* 96.6(1995):1251-1261.

Maas-Szabowski et al. "Keratinocyte Growth Regulation in Defined Organotypic Cultures Through IL-1-Induced Keratinocyte Growth Factor Expression in Resting Fibroblasts." *J. Invest. Dermatol.* 114.6(2000):1075-1084.

Maseesen-Visch. "Atrophie Blanche." *Eur. J. Obstet. Gynecol. Reprod. Biol.* 90.1(2000):1-2.

Metts. "Vulvodynia and Vulvar Vestibulitis: Challenges in Diagnosis and Management." *Am. Fam. Physician.* 59.6(1999):1547-1556.

Moulin et al. "Fetal and Adult Human Skin Fibroblasts Display Intrinsic Differences in Contractile Capacity." *J. Cell. Physiol.* 188(2001):211-222.

Nemecek et al. "Safety Evaluation of Human Living Skin Equivalents." *Toxic. Path.* 27.1(1999):101-103.

Pandya et al. "Disorders of Hyperpigmentation." *Dermatol. Clin.* 18.1(2000):91-98.

Parenteau et al. "The Organotypic Culture of Human Skin Keratinocytes and Fibroblasts to Achieve Form and Function." *Cytotechnology.* 9.1-3(1992):163-171.

Rager et al. "Cutaneous Melanoma: Update on Prevention, Screening, Diagnosis, and Treatment." *Am. Family Physician.* 72.2(2005):269-276.

Southwood et al. "Instrument Sterilization, Skin Preparation, and Wound Management." *Vet. Clin. North Am. Equine Pract.* 12.2(1996):173-1974.

\* cited by examiner

EPITHELIUM

DERMAL LAYER

OUTSIDE ABSCESS WITH GRAFT POSITIONED

STITCHING AND BANDAGES IN PLACE

1 WEEK LATER WITH COMPLETE CLOSING
AND ELIMINATION OF ABSCESS (ULCER)

WOUND INCORPORATING FULL KNEE SURFACE
AND PENETRATING THROUGH TO THE BONE

INSERTION OF BI-LAYER GRAFT
MUSCLE (INTERNAL) AND SKIN (EXTERNAL)

PLACEMENT OF COVER
BANDAGE WITH STAPLES

WOUND 2 DAYS LATER WITH ONLY
SURFACE INVOLVEMENT REMAINING

*PATIENT HAS EXTREME ALLERGIES; 3-4 MONTHS TO FIND BANDAGES; 2-3 MONTHS TO CONVINCE TO CLEAN FIBRIN; ALL RESULTING IN SLOW BUT STEADY TISSUE REPAIR

COMPOSITIONS FOR THE TREATMENT OF SKIN CONDITIONS, DISORDERS OR DISEASES AND METHODS OF MAKING AND USING THE SAME

RELATED APPLICATIONS

This application is a continuation-in-part of U.S. Ser. No. 10/361,450, filed Feb. 10, 2003, now U.S. Pat. No. 8,394,371, which claims the benefit of U.S. Ser. No. 60/356,034, filed Feb. 11, 2002, each of which is incorporated by reference herein in its entirety.

FIELD OF THE INVENTION

The present invention relates generally to methods and compositions designed for treating a subject suffering from a skin condition, disorder or disease. The compositions include undifferentiated fetal skin cells that are either integrated with a collagen matrix or combined with a carrier.

BACKGROUND OF THE INVENTION

Wounds (i.e., lacerations, opening, or ulcers) can be either acute or chronic. Acute wounds are typically sharp injuries to the skin involving little tissue loss. Most acute wounds are closed and are healed by bringing the wound edges together. Chronic wounds are wounds that fail, or are slow, to heal completely. Examples of chronic wounds include pressure sores (decubitus ulcers), diabetic skin ulcers, venous stasis ulcers, burn injury and defects arising following tumor excision.

The cellular morphology of a wound consists of three distinct zones: a central wound space, a gradient zone of local ischemia, and an area of active collagen synthesis. Despite the need for more rapid healing of wounds (i.e., severe burns, surgical incisions, lacerations and other trauma), to date there has been only limited success in accelerating wound healing with pharmacological agents.

The primary goal in the treatment of wounds is to achieve wound closure. Open cutaneous wounds represent one major category of wounds, which includes acute surgical and traumatic wounds, e.g., chronic ulcers, burn wounds, as well as chronic wounds such as neuropathic ulcers, pressure sores, arterial and venous (stasis) or mixed arterio-venous ulcers, and diabetic ulcers. Typically, these wounds heal according to the following process: i) inflammation, ii) fibroblast proliferation, iii) blood vessel proliferation, iv) connective tissue synthesis, v) epithelialization, and vi) wound contraction. Wound healing is impaired when these components, either individually or as a whole, do not function properly. Factors that can affect wound healing, include malnutrition, infection, pharmacological agents (e.g., cytotoxic drugs and corticosteroids), diabetes, and advanced age. See Hunt et al., in Current Surgical Diagnosis & Treatment (Way; Appleton & Lange), pp. 86-98 (1988).

Many different products and protocols are available to treat chronic wounds. See for example Jones et al., in British Journal of Plastic Surgery 55:185-193, 2002, which is incorporated by reference in its entirety. These include simple bandages (notably compression bandages), foams and films, gels and colloids, and pharmaceutical products, such as growth factors. Typically wound healing with a moist occlusive dressing is used rather than using dry, non-occlusive dressings. See Winter, Nature 193:293-94 (1962). Today, numerous types of dressings are routinely used in wound healing. These include films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (nonwoven composites of fibers from calcium alginate), and cellophane (cellulose with a plasticizer). See Kannon et al., Dermatol. Surg. 21:583-590 (1995); Davies, Burns 10:94 (1983). Certain types of wounds (e.g., diabetic ulcers, pressure sores) and the wounds of certain subjects (e.g., recipients of exogenous corticosteroids) do not heal in a timely manner (or at all) with the use of these wound dressings.

Research has shown that the majority of ulcers can be induced to heal by the application of adequate levels of sustained graduated compression. For patients with venous disease, the application of graduated external compression, by forcing fluid from the interstitial spaces back into the vascular and lymphatic compartments, can help to minimize or reverse skin and vascular changes attributed to blockage or damage to the venous system. There are three types of bandages that are commonly used:

Type I: Lightweight Conforming-stretch Bandages:

These bandages include products which have a simple dressing retention function, and they should conform well to a limb or joint, without restricting movement.

Type II: Light Support Bandages:

These bandages include products used to prevent the formation of edema and to give support in the management of mild sprains and strains.

Type III: Compression Bandages:

These bandages include products which rely on the application of pressure. They are most commonly employed to control edema and reduce swelling in the treatment of venous disorders of the lower limbs. Compression bandages have been divided into four groups according to their ability to produce predetermined levels of compression.

Type IIIa: Light compression bandages are able to provide and maintain low levels of pressure, up to 20 mmHg on an ankle of average dimensions. The clinical indications for products of this type include the management of superficial or early varices, and varicosis formed during pregnancy. In general, they are not suitable for controlling or reducing existing edema, or for applying even low levels of pressure to very large limbs.

Type IIIb: Moderate compression bandages are used to apply compression on the order of 30 mmHg on an ankle of average dimensions. They are indicated for the treatment of varicosis during pregnancy, varices of medium severity, the prevention and treatment of ulcers and the control of mild edema.

Type IIIc: High compression bandages may be used to apply high levels of compression on the order of 40 mmHg on an ankle of average dimensions. Indications for these bandages include the treatment of gross varices, post-thrombotic venous insufficiency, and the management of leg ulcers and gross edema in limbs of average circumference. Products in this category are not necessarily able to achieve these levels of pressure on very large limbs that have been further enlarged by the presence of edema.

Type IIId: Extra-high performance compression bandages are capable of applying pressures in excess of 50 mmHg. The power in these bandages is such that they can be expected to apply and sustain these pressures on even the largest and most edematous limbs for extended periods of time.

Additionally, several pharmaceutical modalities (e.g., administration of zinc sulfate, vitamins A, C, and D, calcium, magnesium, copper and iron), have also been utilized in an attempt to improve wound healing. However, except in very limited circumstances, the promotion of wound healing with these agents has met with little success.

In the mid-1980s, Dr. Howard Green conceived a method for growing human skin cells such as keratinocytes. See Green et al. (1979) Proc. Natl. Aced. Sci. 76:5665. Epicel™, a product based on these methods, is used to treat deep wounds that require grafting (skin replacement), such as those that occur with severe burns. However, because Epicel™ only replaces the lost epidermal layer, it works best in combination with something that restores the dermal layer of the skin. In fact, Epicel™ is not an artificial skin, but rather is a method in which a new epidermis layer is "grown to order" in a laboratory from surgically harvested skin cells taken from an unburned area of the patient. Thus, Epicel™ functions as an autologous graft. See U.S. Pat. Nos. 4,016,036 and 4,304,866.

In very severely burned patients who have little or no remaining intact skin, artificial skin is an extremely useful material that not only covers and protects the wounded area, but that also promotes re-growth of a natural skin rather than of scar tissue.

Many new artificial skins initially used skin from related donors (such as family members having similar genetic markers). However, doing so required the coadministration of powerful immunosuppressant drugs to dampen the patient's immune system so that the graft would not be rejected. Crippling the patient's immune system in this way can pose additional, serious problems for the patient. Instead, the patient's own unburned skin (often from the scalp, which is rarely burned) is commonly used as a source of graft material.

However, using such skin grafts (or even skin taken from cadavers) does not permanently solve the problems. There is also a need for some type of artificial means to recover skin. Using a synthetic product would also offer an advantage in that such a material is free of viruses, bacteria and other pathogens, which can transmit disease.

For example, Ethicon Inc., a Johnson & Johnson company, obtained exclusive marketing and distribution rights to Integra®, a product which contains no living components, and is not itself actually designed to be a replacement skin. Rather, it provides a protective covering as well as a pliable scaffold onto which the patient's own skin cells can "regenerate" the lower, dermal layer of skin destroyed by a burn. See U.S. Pat. No. 5,489,304. Just as living skin is structured, Integra® consists of two layers. The bottom layer, which is designed to "regenerate" the lower, dermal layer of real skin, is composed of a matrix of interwoven bovine collagen and a glycosaminoglycan that mimics the fibrous pattern of dermis. This matrix is then affixed to a temporary upper layer, a medical-grade, flexible silicon sheet that mimics the epidermal, or surface, layer of skin. Integra® is draped over the wound area and is kept there for 2 to 4 weeks, during which time the patient's own cells make their way into the matrix and create a new dermis. The top layer of Integra® is then removed, and a very thin sheet of the patient's own epithelial cells are then applied. Over time, an epidermal layer is reconstructed from these cells.

AlloDerm™, another product on the market, is sold and manufactured by LifeCell Corporation of The Woodlands, Texas. It is produced by removing from cadaver skin all cell components that cause a burn patient's immune system to reject a graft from any other person. A key feature of this process is the preservation, to the greatest extent possible, of the "natural," three-dimensional structure of the dermis. Properly approximating this scaffold, whether from real dermis (as in AlloDerm™) or artificial dermis (as in Integra®), is crucial to the ability of the patient's remaining cells to regenerate themselves into a new, functioning skin.

Dermagraft (Advanced Tissue Sciences) is a product which is grown under laboratory conditions from human stromal cells (e.g., fibroblasts from neonatal tissue) seeded onto a biocompatible, chemical base known as a scaffold. See U.S. Pat. No. 5,460,939. Typically, such scaffolds are made of polyglycolic acids, which are the basis of many "resorbable" medical materials, such as surgical sutures and surgical glues. When applied to the body, the scaffold breaks down into glycolic acid and lactic acid, which are carried away by the bloodstream and metabolized to carbon dioxide, oxygen, and water.

Another tissue engineered skin, Apligraf®, manufactured by Organogenesis, is a living two-layer skin substitute that mimics the epidermal and dermal layers of skin. Apligraf® is made with two types of living human skin cells—epidermal keratinocytes and dermal fibroblasts. Moreover, Apligraf®, delivers additional cytokines and growth factors not provided by a dermal layer alone. See U.S. Pat. No. 4,837,379.

The current techniques and applications described above all lack certain important characteristics. It is therefore an object of the present invention to provide a three-dimensional cutaneous tissue allograft construct that will overcome one or more of the abovementioned problems.

What is needed is a safe and effective, means for enhancing the healing of wounds that can be used without regard to the type of wound or the nature of the patient population.

SUMMARY OF THE INVENTION

The present invention provides three-dimensional cutaneous tissue allograft constructs containing undifferentiated fetal skin cells integrated with a collagen matrix or a composition comprising a carrier and undifferentiated fetal skin cells, where the fetal skin cells comprise undifferentiated dermal fibroblasts, for preventing or treating a skin condition, disorder or disease in a subject without scar formation upon topical administration, where the undifferentiated fetal skin cells are from donor tissue of 12-16 weeks gestation. In one embodiment, the collagen matrix of the construct is a human collagen matrix. In another embodiment, the collagen matrix of the construct is a horse collagen matrix. In one embodiment, the cells of the construct are human fetal skin cells. In another embodiment, the cells of the construct are horse fetal skin cells.

The present invention also provides a composition comprising a carrier and undifferentiated fetal skin cells, where the fetal skin cells comprise undifferentiated dermal fibroblasts, in the form of a cream for a topical administration for preventing or treating a skin condition, disorder or disease in a subject without scar formation upon topical administration, where said undifferentiated fetal skin cells are from donor tissue of 12-16 weeks gestation. In one embodiment, the collagen matrix of the construct is a human collagen matrix. In another embodiment, the collagen matrix of the construct is a horse collagen matrix. In one embodiment, the cells of the construct are human fetal skin cells. In another embodiment, the cells of the construct are horse fetal skin cells.

In one aspect, the cream comprises 68.51% (by weight) water, 10.0% (by weight) hydrogenated vegetable oil, 5.0% (by weight) glycerin, 4.9% (by weight) propylene glycol, 2.0% (by weight) cetearyl octanoate, 1.35% (by weight) cetearyl alcohol, 0.7% (by weight) hydrolyzed glycosaminoglycans, 0.7% (by weight) PEG-8 C12-18 ester, 0.7% (by weight) cetyl alcohol, 0.7% (by weight) cetyl palmitate, 0.7% (by weight) hydrolyzed actin, 0.6% (by weight) hydrolyzed fibronectin, 0.6% (by weight) glyceryl stearate, 0.5% (by weight) hydrolyzed keratin, 0.5% (by weight) fragrance, 0.5% (by weight) PPG-25-Laureth-25, 0.4% (by weight) PEG-5 pentaerythrityl ether, 0.32% (by weight) Ricinoleth-40, 0.3% (by weight) hydroxyethylcellulose, 0.2% (by weight) glucose, 0.2% (by weight) sodium chloride, 0.14% (by weight) methylparaben, less than 0.1% (by weight) simethicone, 0.08% (by weight) ascorbyl palmitate, 0.08% (by weight) tocopheryl acetate, 0.08% (by weight) imidazolidinyl urea, 0.05% (by weight) propylparaben, 0.05% (by weight) potassium chloride, and 0.04% (by weight) magnesium chloride.

The present invention also provides methods for treating a skin condition, disorder or disease in a subject suffering from the skin condition, disorder or disease, by cutaneously administering any composition of the present invention to an affected area of the subject's skin. In one preferred embodiment, the subject is a horse. In another preferred embodiment, the subject is a human.

Examples of skin conditions, disorders or diseases include, but are not limited to, wounds, skin defects and skin conditions. In one embodiment, the wound may be an acute wound. Preferably, the acute wound is selected from the group consisting of minor cuts, burns, dry skin, skin tears, skin lacerations, surgical wounds, accidental trauma and hypertrophic scars. In another embodiment the wound may be a chronic wound. Preferably, the chronic wound is selected from the group consisting of venous ulcers, pressure ulcers, diabetic ulcers, arterial ulcers, burns, and peri-ulcers.

In yet another embodiment, the skin defect may be selected from the group consisting of eczema, psoriases, radiodermatitis, skin cancer, urticaria, livedoid vasculitis, severe dryness, Atrophie blanche, vestibulitis, blemishes, age spots, scars, bruises, birthmarks, tattoos, hyperpigmentation, atrophic dermatitis, severely creviced and chapped hands, and keloids.

In another embodiment, the skin condition is an inflammatory skin condition. Preferably, the inflammatory skin condition is selected from the group consisting of blemishes, age spots, scars, burns, bruises, birthmarks, tattoos, hyperpigmentation, atopic dermatitis, peri-ulcers, eczema, radiodermatitis, ulcers, urticaria, severe dryness, Atrophie blanche and vestibulitis.

In a preferred embodiment, the skin condition is a peri-ulcer. In another preferred embodiment, the skin condition is Atrophie blanche. In yet another preferred embodiment, the skin condition is hyperpigmentation. Alternatively, the skin condition is vestibulitis.

DETAILED DESCRIPTION OF THE INVENTION

Figure 1:
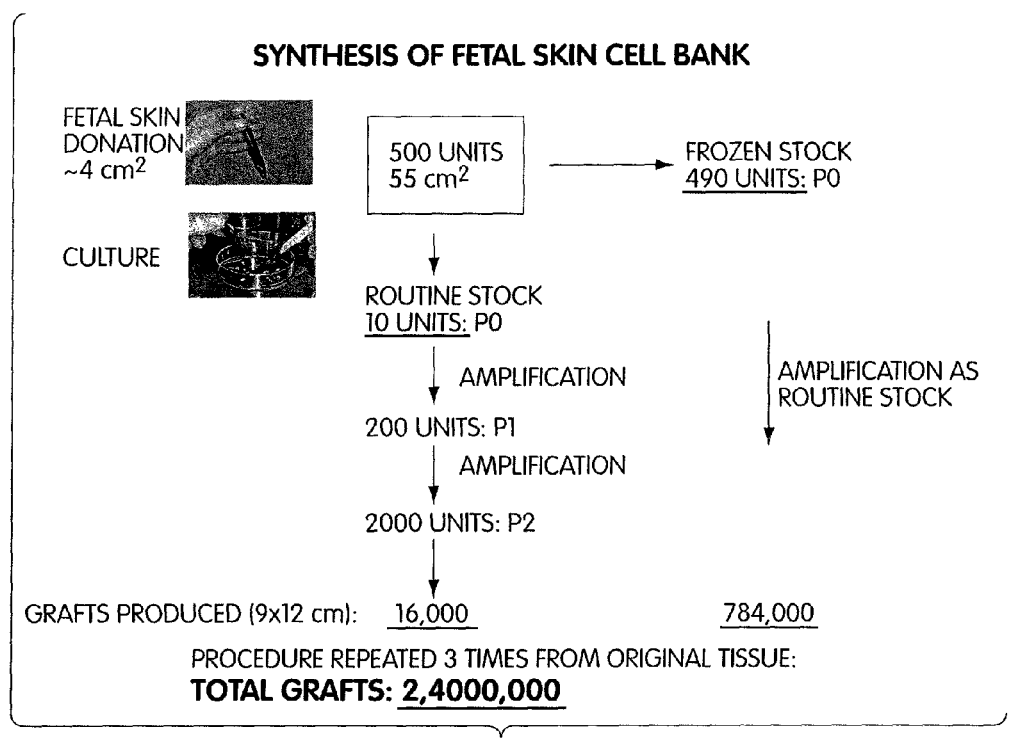
FIG. 1 is a schematic, which shows the synthesis of a fetal cell bank.

The fields of tissue engineering and material science are rapidly producing novel biomaterials with remarkable biological functions. The mechanical properties of these new materials can be tailored for specific applications and the cells that populate them can form actual tissues for maintenance, restoration or amelioration of function. Therefore, the origin of the cells and their interaction with a biomaterial is extremely important for eventual therapeutic usage.

Fundamental differences between fetal and adult skin and the fetal and adult skin wound environments may be important in inducing scar-free tissue repair. Early in gestation, the dermis is thin, relatively acellular and a low extracellular matrix is present. During further development, dermal collagen is deposited and sulfated glycosaminoglycans (GAGs) replace hyaluronic acid (HA) among other non-sulfated GAGs. The extremely rapid growth and the loose extracellular matrix provide a conductive territory for scar-less fetal skin repair.

Studies suggest that fetal skin cells themselves are responsible for scar-free tissue repair, since the in utero environment seems to be neither essential nor sufficient for scar-less fetal repair. As demonstrated in an opossum model, fetal skin outside the warm, sterile, growth factor rich amniotic environment has been shown to be very efficient in healing scarlessly and rapidly. This marsupial is born fetal-like, both physiologically and anatomically, and remains attached to the mothers nipple for 4 to 5 weeks (Armstrong et al., Dev. Biol. 169: 242-260, 1995). Despite their extrauterine location, wounds in early-pouch young re-epithelialize very quickly, synthesize collagen and heal without scars. In contrast, wounds in older-pouch young heal more slowly and exhibit scar formation.

Similarly, human fetal skin transplanted subcutaneously to an immunoincompetent mouse retained its developmental characteristics and healed scarlessly with restoration of hair follicles and reticular collagen arrangement (Lorenz et al., Development 114: 253-259, 1992). As the regenerative capabilities of human fetal skin were not disrupted by an adult extrauterine wound environment or by contact with adult mouse blood, the scar-less capacities appear to be intrinsic to the fetal tissue itself.

An important advantage of using fetal cells for therapeutic reasons is that fetal tissue is preimmunoincompetent and associated with a reduced capacity to evoke an immunological response in the recipient of such cells. This decreased immunocompetence is associated with the lack of post-thymic T-lymphocytes prior to 14 weeks of gestation (Crombleholme et al., Am J Obstet Gynecol 164: 218-230, 1991; Gabbianelli et al., J. Immunol. 144: 3354-3360, 1990).

Engineering of fetal tissue has a high potential for the treatment of skin conditions, disorders or diseases of the skin in mammals. By exploiting the potential for fetal skin expansion under certain culture conditions and within certain associated bioengineered matrices, large numbers of skin cells can be frozen for therapeutic usage, and hundreds of thousands of subject's may be treated from a single organ donation.

The constructs and compositions of the present invention are ideal for repairing, treating, and/or preventing symptoms of skin conditions, disorders or diseases. Unlike autografts, the methods and compositions of the present invention do not require a donor site biopsy, which is important for young children or burn patients who do not have much skin tissue to spare. Moreover, the constructs and compositions are immediately available, unlike autograft procedures which can take up to 3 or 4 weeks to produce. Further, these constructs and compositions can be delivered immediately and in unlimited quantities.

There has been little research on expanding fetal tissue with cell culture and association into matrices or membranes. Using the methods described herein, it is possible to have stringently controlled fetal skin cells and expand them into very large cell banks (e.g., one organ donation of 4 $cm^2$ can produce ~2,400,000 skin grafts of ~10 $cm^2$ per graft). Advantages of using fetal skin cells include, but are not limited to 1) their ability to be up to three times more resistant to Ultraviolet A (UVA) radiation and up to two times more resistant towards hydrogen peroxide treatment, as compared to adult cells; 2) their ability to induce scar-free tissue repair, an intrinsic property of fetal tissue itself which seems to be related to the protein composition at different ages of development (Lorenz et al., Development 114: 253-259, 1992) and 3) the fact that they are pre-immunocompetent and are associated with a reduced capacity to evoke an immunological response in the recipient of such cells. Fetal cell lines have not previously been used or developed for tissue engineering purposes.

The present invention relates generally to a three-dimensional cutaneous tissue allograft construct containing undifferentiated fetal cells and collagen for the treatment of skin conditions, disorders or diseases. Additionally, the invention relates to a composition containing one or more undifferentiated fetal cells and/or one or more fetal proteins and a carrier. The invention also provides methods, processes of making such compositions and constructs, as well as methods of use thereof.

It is to be understood that the terminology used herein is for the purpose of describing particular embodiments only and is not intended to limit the scope of the present invention.

As used herein and in the claims, the singular forms "a," "and" and "the" include plural referents unless the context clearly dictates otherwise.

The term "undifferentiated" is used herein to describe an immature or primitive cell. For example, undifferentiated fetal skin cells include those that can differentiate into dermal fibroblasts and epidermal keratinocytes.

The term "integrated" or "integrated with" is used to describe any means of blending, particularly those relating to adding cells to a matrix. The term includes, but is not limited to mixing, combining, pipetting, seeding, plating or placing.

The term "appropriate culture conditions" is a medium for culturing cells containing nutrients that promote proliferation. The nutrient medium may contain any of the following in an appropriate combination and in the appropriate concentrations: isotonic saline, buffer, amino acids, serum or serum replacement, and other exogenously added factors. Those skilled in the art will recognize that any commonly employed culture conditions can be used.

The term "collagen" refers to a polypeptide compound, which is hydrophilic in nature, that is subject to degradation by extracellular enzymes. Because, this substance is well studied, many key parameters can be controlled. Collagen is a weak antigen, thereby resulting in minimal rejection potential. A preferred collagen used in the constructs, methods, and compositions of the invention is horse collagen.

The term "cell line" refers to a permanently established cell culture that will proliferate indefinitely given appropriate fresh medium and sufficient space.

The term "cell bank" refers to harvesting biopsies from donor fetal tissue; growing the fetal tissue and proliferating undifferentiated fetal cells to a high concentration under appropriate culture conditions; trypsinizing the tissue and cells of the resulting cultures to allow their suspension; pooling the suspended cells to make a generally uniform suspension of cells from the culture; gently mixing with a cryoprotectant; sealing aliquots of the cell suspension in ampoules; and freezing the aliquots (e.g., by decreasing the temperature of the ampule by 1° C./min until −80° C. and then transferred to −160° C. approximately 24 hours later). This ultra-cold temperature bank preserves the cells such that they stop aging, thereby allowing them to retain the function and activity they had on the day they were collected.

The term "treating" (as in "treating a skin condition, disorder or disease") includes (1) preventing the condition, i.e., avoiding any clinical symptoms of the condition, (2) inhibiting the condition, that is, arresting the development or progression of clinical symptoms, and/or (3) relieving, repairing, or reversing the condition, i.e., causing regression of clinical symptoms.

The terms "condition," "disorder" and "disease" are used interchangeably herein to refer to physiological states that can be prevented or treated by administration of an active agent as described herein. Examples of skin conditions, disorders and diseases include, but are not limited to, minor cuts, burns, dry skin, skin tears, skin lacerations, surgical wounds, accidental trauma, hypertrophic scars, venous ulcers, pressure ulcers, diabetic ulcers, arterial ulcers, eczema, psoriases, radiodermititis, skin cancer, urticaria, livedoid vasculitis, Atrophie blanche, blemishes, age spots, scars, bruises, birthmarks, tattoos, hyperpigmentation, atopic dermatitis, peri-ulcers, eczema, radiodermititis, ulcers and urticaria.

The term "wound" refers broadly to injuries to the skin and subcutaneous tissue initiated in any one of a variety of ways (e.g., pressure sores from extended bed rest, wounds induced by trauma, cuts, ulcers, burns and the like) and with varying characteristics. Wounds are typically classified into one of four grades depending on the depth of the wound: (i) Grade I: wounds limited to the epithelium; (ii) Grade II: wounds extending into the dermis; (iii) Grade III: wounds extending into the subcutaneous tissue; and (iv) Grade IV (or full-thickness wounds): wounds wherein bones are exposed (e.g., a bony pressure point such as the greater trochanter or the sacrum).

The term "acute wound" refers to a sharp insult or injury to the skin involving no tissue loss, severe symptoms and having a short course. Examples of acute wounds include, but are not limited to, minor cuts, burns, dry skin, skin tears, skin lacerations, surgical wounds, accidental trauma and hypertrophic scars.

The term "chronic wound" refers to a wound that has not healed within approximately thirty days. Examples of chronic wounds include, but are not limited to, venous ulcers, pressure ulcers, diabetic ulcers, arterial ulcers and burns.

The term "healing" in respect to a wound refers to a process to repair a wound, as by scar formation.

The phrase "inducing or accelerating a healing process of a skin wound" refers either to the induction of the formation of granulation tissue of wound contraction and/or to the induction of epithelialization (i.e., the generation of new cells in the epithelium). Wound healing is conveniently measured by a decrease wound area.

The term "subject" (as in treatment of "a subject") is intended to refer to a mammalian individual afflicted with, prone to, or suffering a condition, disorder or disease (as specified herein). This term includes both humans and animals. For example, the subjects can be, e.g., humans, non-human primates, wildlife, dogs, cats, horses, cows, pigs, sheep, rabbits, rats, or mice. As used herein, the term wildlife includes any mammals, birds or fish that are not domesticated. Examples of such wildlife include, but are not limited to, badgers, beavers, lions, tigers, bears, hawks and deer.

As used herein a "composition" of the invention may contain one or more undifferentiated fetal cells along with other chemical components including, but not limited to, traditional drugs, physiologically suitable carriers and excipients.

Alternatively, a "composition" of the invention may include one or more undifferentiated fetal cells and/or one or more fetal proteins that have been stabilized, along with other chemical components including, but not limited to, traditional drugs, physiologically suitable carriers and excipients. Such components help to facilitate administration of the protein and/or cell to a subject. The compositions of the present invention may be manufactured by processes well known in the art, e.g., by means of conventional mixing, dissolving, granulating, dragee-making, levigating, emulsifying, encapsulating, entrapping or lyophilizing processes.

Techniques for formulation and administration of active ingredients may be found in "Remington: The Science and Practice of Pharmacy," Lippincott Williams & Wilkins Publishing Co., $20^{th}$ edition, which is incorporated herein by reference.

While various routes for the administration of active ingredients are possible, for the purpose of the present invention, the topical route is preferred, and is assisted by a topical carrier. The topical carrier is one, which is generally suited for topical active ingredients administration and includes any such materials known in the art. The topical carrier is selected so as to provide the composition in the desired form, e.g., as a liquid or non-liquid carrier, lotion, cream, paste, gel, powder, ointment, solvent, liquid diluent, drops and the like, and may be comprised of a material of either naturally occurring or synthetic origin. The selected carrier should not adversely affect the active agent or other components of the topical formulation, which is stable with respect to all components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

Ointments are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols (PEGs) of varying molecular weight. See Remington, supra.

Lotions are preparations to be applied to the skin surface without friction, and are typically liquid or semiliquid preparations in which solid particles, including the active agent, are present in a water or alcohol base. Lotions are usually suspensions of solids, and preferably comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions, as well as compounds useful for localizing and holding the active agent in contact with the skin, e.g., methylcellulose, sodium carboxymethylcellulose, or the like. A particularly preferred lotion formulation for use in conjunction with the present invention contains propylene glycol mixed with a hydrophilic petrolatum such as that which may be obtained under the trademark Aquaphor®, available from Beiersdorf, Inc. (Norwalk, Conn.).

As known in the art, creams containing the active agent are viscous liquid or semisolid emulsions, either oil-in-water or water-in-oil. Cream bases are water-washable, and contain an oil phase, an emulsifier and an aqueous phase. The oil phase is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation, as described in Remington, supra, is generally a nonionic, anionic, cationic or amphoteric surfactant.

Microemulsions are thermodynamically stable, isotropically clear dispersions of two immiscible liquids, such as oil and water, stabilized by an interfacial film of surfactant molecules (Encyclopedia of Pharmaceutical Technology (New York: Marcel Dekker, 2002), $2^{nd}$ Edition). For the preparation of microemulsions, a surfactant (emulsifier), a co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifier") is generally selected from the group of polyglycerol derivatives, glycerol derivatives and fatty alcohols. Preferred emulsifier/co-emulsifier combinations are generally, although not necessarily, selected from the group consisting of: glyceryl monostearate and polyoxyethylene stearate; polyethylene glycol and ethylene glycol palmitostearate; and caprilic and capric triglycerides and oleoyl macrogolglycerides. The water phase can include not only water, but also, typically, buffers, glucose, propylene glycol, polyethylene glycols, preferably lower molecular weight polyethylene glycols (e.g., PEG 300 and PEG 400), and/or glycerol, and the like. The oil phase will generally comprise, for example, fatty acid esters, modified vegetable oils, silicone oils, mixtures of mono- di- and triglycerides, mono- and di-esters of PEG (e.g., oleoyl macrogol glycerides), etc.

Gel formulations are semisolid systems consisting of either suspensions made up of small inorganic particles (two-phase systems) or large organic molecules distributed substantially uniformly throughout a carrier liquid (single phase gels). Single phase gels can be made, for example, by combining the active agent, a carrier liquid and a suitable gelling agent such as tragacanth (at 2 to 5%), sodium alginate (at 2-10%), gelatin (at 2-15%), methylcellulose (at 3-5%), sodium carboxymethylcellulose (at 2-5%), carbomer (at 0.3-5%) or polyvinyl alcohol (at 10-20%) together and mixing until a characteristic semisolid product is produced. Other suitable gelling agents include methylhydroxycellulose, polyoxyethylene-polyoxypropylene, hydroxyethylcellulose and gelatin. Although gels commonly employ aqueous carrier liquid, alcohols and oils can be used as the carrier liquid as well.

Various additives known to those skilled in the art, may also be included in the compositions of the invention. Examples of such additives include, but are not limited to, solubilizers, skin permeation enhancers, opacifiers, preservatives (e.g., anti-oxidants), gelling agents, buffering agents, surfactants (particularly nonionic and amphoteric surfactants), emulsifiers, emollients, thickening agents, stabilizers, humectants, colorants, fragrance, and the like. Inclusion of solubilizers and/or skin permeation enhancers is particularly preferred, along with emulsifiers, emollients and preservatives. Examples of suitable solubilizers include, but are not limited to, the following: hydrophilic ethers such as diethylene glycol monoethyl ether (ethoxydiglycol, available commercially as Transcutol®) and diethylene glycol monoethyl ether oleate (available commercially as Softcutol®); polyethylene castor oil derivatives such as polyoxy 35 castor oil, polyoxy 40 hydrogenated castor oil, etc.; polyethylene glycol, particularly lower molecular weight polyethylene glycols such as PEG 300 and PEG 400, and polyethylene glycol derivatives such as PEG-8 caprylic/capric glycerides (available commercially as Labrasol®); alkyl methyl sulfoxides such as DMSO; pyrrolidones such as 2-pyrrolidone and N-methyl-2-pyrrolidone, and DMA. Many solubilizers can also act as absorption enhancers. A single solubilizer may be incorporated into the formulation, or a mixture of solubilizers may be incorporated therein. Suitable emulsifiers and co-emulsifiers include, without limitation, those emulsifiers and co-emulsifiers described with respect to microemulsion formulations. Emollients include, for example, propylene glycol, glycerol, isopropyl myristate, polypropylene glycol-2 (PPG-2) myristyl ether propionate, and the like.

Other active agents may also be included in the formulation, e.g., anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate).

By the term "effective" or "therapeutically effective" amount of a composition is meant a nontoxic, but sufficient, amount that provides the desired effect at a reasonable benefit/risk ratio attending any medical treatment. The desired effect can be alleviation or prevention of the signs, symptoms, or causes of a disease, or any other desired alteration of a biological system.

One skilled in the art will realize that the undifferentiated fetal cells used to make the three-dimensional cutaneous tissue allograft and composition of the invention may include fetal skin cells, for skin grafts and fetal muscle cells, for muscle grafts; and fetal bone cells, for bone grafts.

In one aspect, the invention provides a three-dimensional cutaneous tissue allograft construct containing undifferentiated fetal cells integrated with a collagen matrix (e.g., horse collagen). For example, the undifferentiated fetal cells may be fetal skin cells such as those that are able to differentiate into dermal fibroblasts and epidermal keratinocytes under appropriate culture conditions. Integration can be accomplished by any means known to those skilled in the art, including but not limited to, mixing, combining, pipetting, seeding, plating, or placing. This construct can then be used to treat a subject suffering from a skin condition, disorder or disease.

To create cell banks of cultured, undifferentiated fetal cells, biopsies from fetal tissue are obtained immediately following pregnancy interruption in accordance with the procedures and policies of the Ethics committee of the CHUV. Collected donor tissue is of 12-16 weeks gestation. The fetal tissue is divided into small fragments in multiple 10 cm$^2$ tissue culture plates, and is grown in Dulbecco's MEM (DMEM) tissue culture media with glutamine. Fetal serum is then added to the plates. When cell growth advances, e.g., after about one week, the tissue and cells are trypsinized. Some of the plates are then frozen into individual units, e.g. in liquid nitrogen. Cells are then centrifuged and resuspended to produce a generally uniform suspension of cells from the culture.

Next, the cells are gently mixed with a cryoprotectant (for example DMEM, 5 ml+fetal calf serum, 4 ml+dimethylsulfoxide, 1 ml (DMSO)). The cell suspensions are then sealed in aliquots, and frozen, e.g. in liquid nitrogen. In one preferred embodiment, the aliquots are frozen at the rate of 1° C./min until they reach a temperature of −80° C. and then transferred to −160° C. approximately 24 hours later. Aliquots of homogeneous banked cells can then be used for any desired purpose such as production of the three-dimensional cutaneous tissue allograft construct and/or the composition of the invention, or for use in the manufacture of a medicament for treating skin conditions, disorders or diseases, by unsealing an ampoule of the cell bank, thawing the contents, and transfer into ordinary cell culture medium.

The three-dimensional cutaneous tissue allograft of the invention can be produced as follows: Three to five days prior to the grafting date, 9×12 cm sheets of equine collagen are seeded with the fetal skin cells from the cell bank, e.g. about $1 \times 10^5$ cells/cm² (cells used from passages 0 to 3), by making small incisions into the matrix with sterile, small-bored pipette tips. Medium is then added to the culture plate some time later (e.g., approximately 1 hour). The medium is also changed on a periodic basis, such as once every two days.

The construct that is produced contains undifferentiated epidermal keratinocytes (about 10% to about 13.5%) and undifferentiated dermal fibroblasts (about 90% to about 86.5%). Because of the three-dimensional structure of this graft, it is very easy to apply the grafts in any orientation on a patient or subject, which is advantageous, since many skin conditions, disorders or diseases, exist in areas of the body that are typically difficult to cover with grafts currently used by those skilled in the art.

Without being limited by any particular mechanism, it is likely that the cells of the allograft constructs are able to exert promoting effects on adhesion, proliferation and migration of existing cells by the secretion of growth factors available in fetal cells. Repaired wounds tend to heal with no remaining scar and the skin appearing much less atrophic. Practical advantages of this technique include the fact that it is non-invasive, and, therefore, it does not require surgical facilities. These treatment methods are easily applied in an ambulatory manor and the cells are immediately available instead of in 4-6 weeks, as with traditional autograft techniques. Finally, since these constructs can be used to treat even the most resistant ulcers with a very high success rate, this technique will be useful for treatment of acute wounds in order to repair the skin into a "perfect state".

The invention also provides a composition containing undifferentiated fetal cells and/or proteins and a carrier. This composition can be used to treat a number of skin defects, including, but not limited to blemishes, age spots, scars, burns, bruises, birthmarks, tattoos, pigmentation problems, peri-ulcers, eczema, radiodermititis, ulcers, urticaria, severe dryness, and Atrophie blanche.

In order to make the composition, biopsies from fetal donor tissue can be obtained and cell lines developed as described above. For example, the fetal tissue can be divided into small fragments in multiple 10 cm² tissue culture plates, which have been prepared with grid incisions made by a scalpel. DMEM tissue culture media with glutamine and 10% fetal serum is added to the plates. The fetal cells remain in the undifferentiated state, and are expanded in high concentration to create a cell bank from which fetal skin grafts are derived. Cells are then frozen in a mixture of DMSO, DMEM and fetal serum until they are needed.

Cells from passages 5-10 are prepared at a concentration of about $5.3 \times 10^3$ cells/ml. This concentration may vary depending on the type of skin defect and whether the patient is an adult or child. For example, the concentration of cells can range from about $5.3 \times 10^2$ cells/ml to about $5.3 \times 10^4$ cells/ml. The fetal proteins are then stabilized and are incorporated into a carrier, either alone or in combination with the fetal cells.

The composition described above can be used to prevent or treat a skin condition, disorder or disease by administering a therapeutically effective amount of the composition to the susceptible or affected area of a subject's skin. For example, the skin condition, disorder or disease includes, but is not limited to, an inflammatory skin condition. Examples include, but are not limited to, blemishes, age spots, scars, burns, bruises, birthmarks, tattoos, hyperpigmentation, atopic dermatitis, peri-ulcers, eczema, radiodermititis, ulcers, urticaria, severe dryness and Atrophie blanche. The subject includes both humans and animals. For example, the subjects can be, e.g., humans, non-human primates, wildlife, dogs, cats, horses, cows, pigs, sheep, rabbits, rats, or mice.

Those skilled in the art will realize that any suitable carrier and/or stabilizer can be used with the compositions of the invention. For example, in a preferred embodiment, the carrier is a topical cream.

The three-dimensional cutaneous tissue allograft construct of the invention can be used alone or in combination with the composition of the invention. For example, the allograft construct and the composition can be administered simultaneously or sequentially.

Table 1 lists a number of conditions that can be treated using the fetal cell therapies of the invention. The table also details the number of patients having each condition that were treated as well as the results observed.

TABLE 1

Skin Pathologies Treated with Fetal Cell Therapy

Eczema

5 Patients treated, each had complete elimination of eczema.
Atrophie Blanche

3 Patients treated, amelioration and stabilization of Atrophie blanche.
Burns

7 Patients treated, pain and total skin reconstitution noticed.
Scar Management

4 Patients treated, with good results
Severely Creviced and Chapped Hands

10 Patients treated, good amelioration and skin stabilized, complete healing.
Radiodermatitis 2 Patients treated, extremely good progress, reinforced skin, and less sensitive.
Psoriasis 3 Patients treated, 1 is completely healed, 2 have less itching, pinpoint irritation remaining.
Keloids 1 Patient treated, large irritated keloid more than half the size and all itching stopped.
Vestibulitis 2 Patients treated, all itching stopped.
Atopic Dermatitis-Dryness 4 Patients treated, stabilization of the skin and all itching and dryness was eliminated.

The following Examples are presented in order to more fully illustrate the preferred embodiments of the invention. These Examples should in no way be construed as limiting the scope of the invention, as defined by the appended claims.

EXAMPLES

Example 1

Harvesting of Fetal Skin

Biopsies were obtained from donor tissue of fetal skin immediately following pregnancy interruption in accordance with the policies and procedures of the Ethics committee of the CHUV. Donor tissue is of 12-16 weeks gestation.

Example 2

Fetal Skin Cell Bank Synthesis

From the original biopsy, described in Example 1, 500 10 cm plates were seeded with whole tissue fragments approximately 10 per plate (<0.5 mm$^3$). These fragments were grown in DMEM supplemented with only 10% fetal bovine serum (Hyclone). When cell growth advanced after approximately 1 week, dishes of tissue and cells were trypsinized (0.25% trypsin-0.1% ethylene diaminetetraacetic acid [EDTA]). At this point, 490 plates were frozen into individual units in liquid nitrogen. Cells were centrifuged at 2000 g for 15 min and resuspended in a freezing solution of DMEM (5 ml)+FCS (4 ml)+DMSO (1 ml, Fluka) and frozen in one ml aliquots (~3 million cells) at −80° C. in Nalgene™ Cryo 1° C. Freezing Container's (Nalgene) to achieve a −1° C./min rate of cooling and freezing curves. After 24 hours, cells were transferred to liquid nitrogen for longer storage. Cells stored in this manner are capable of being stored for at least 10 years. Ten plates were amplified to 200 plates and further amplified to 2000 units for the frozen stock. Cell cultures were grown at 37° C. in a humidified atmosphere of 95% air/5% $CO_2$. (See FIG. 1).

With one organ donation of 1-4 cm$^2$ of fetal skin, it is possible to develop a skin cell bank capable of producing a minimum of 2,400,000 skin grafts (9×12 cm) for therapeutic use. The fetal skin cells are routinely tested for *Mycoplasma* as well as for all bacterial and fungal infections. For the original tissue donation, the patient was tested at 0 and 3-6 months using the antibodies listed in Table 2:

TABLE 2

| Antibodies Tested | Company |
| --- | --- |
| HBsAg-Cobas Core HbsAgII EIA | F. Hoffmann-La Roche AG |
| Anti-HIV-1/HIV-2 | F. Hoffmann.La Roche AG |
| Cobas Core Anti-HIV-1/HIV-2 EIA DAGS II | F. Hoffmann.La Roche AG |
| Anti HCV-Cobas Core Anti-HCV EIA | F. Hoffmann-La Roche AG |
| AXSym Anti-HCV EIA, Version 3.0 | Abbott BmbH Diagnostika |
| PCR-HCV-Cobas Amplicor, Version 2.0 | F. Hoffmann-La Roche AG |
| Treponema pallidum: Serodia-TP.PA | Fujirebio, Almedica AG |
| Anti-CMV-Vidas CMV IgG | BioMérieux SA |
| ETI-CYTOK-M reverse | Sorin Diagnostics S.r.L |
| Toxoplasma gondii-Toxo-Screen DA (IgG), | BioMérieux SA |
| Toxo-ISAGA (IgM) | BioMérieux SA |

The fetal tissue was also examined in the pathology lab for any genetic and/or pathological abnormalities.

Example 3

Radiation Sources, Exposure Conditions and Chemical Treatments

In order to determine the resistance of fetal and adult skin cells to physical and oxidative stress, a series of experiments looking at UVA radiation and hydrogen peroxide treatment as the source of stress were done.

The UVASUN 3000 lamp (Mutzhas, Munich, Germany) emits wavelengths between 330 and 450 nm at a dose rate of 300 W/m$^2$ at a convenient irradiation position. The spectral output of the lamp was analyzed with a calibrated Optronic model 742 spectroradiometer (Optronics Laboratories, Penn., USA) and showed a broad peak between 360 and 410 nm. The UVASUN 3000 lamp is equipped with an infrared filter and a filter that cuts off sharply all wavelengths below 335 nm. In addition, cells were irradiated with plastic tissue culture lids that permit no transmission of UVB or UVC radiations. Radiation dosages were monitored by International Light Radiometer, IL 1700 with UVA detector head, calibrated against the spectroradiometer.

Fetal skin biopsies were obtained from donors immediately following pregnancy interruption in accordance with the procedures and policies of the Ethics committee of the CHUV. Donor tissue was of approximately 12-16 weeks gestation.

Skin samples from adult donors (SW2, 24 yr old male; SW12, 39 yr old female; GT, 27 yr old male) were obtained in the Department of Dermatology in the Lausanne University Hospital from non-sun-exposed skin sites with informed consent and approval from the Medical School Ethics Committee.

Epidermal Keratinocyte Culture:

Skin samples were washed three times for ten minutes each in PBS containing penicillin (100 U/ml) and streptomycin (100 μg/ml). Tissue was treated for ~15 minutes with trypsin/EDTA and the epidermal cell layer scraped gently away from the dermal tissue with the aid of a dissecting microscope. The epidermal tissue was fragmented and centrifuged at 2000 g for 15 minutes. The pellet was then transferred to small tissue culture flasks which contained γ-irradiated (2500 rads) Swiss mouse 3T3 cells at 70% confluence and keratinocyte complete medium as follows: Dulbecco's minimal essential medium:Hams diluted 3:1 (Flow); 10% FCS; 1% glutamine; 0.4 μg/ml hydrocortisone; 10-10 M cholera toxin; 5.0 mg/ml insulin; 1.2 mg/ml adenine; 2.5 mg/ml transferrin; 0.14 mg/ml triiodothyronine; 10 μg/ml epidermal growth factor. Keratinocytes were grown at 37° C. in a humidified atmosphere with 90% ait/10% $CO_2$. Cells used for human skin grafts were grown in serum-free medium (Gibco, keratinocyte SFM) and for the first 12 hours, 5% FCS was added to assure higher cell attachment.

Dermal Fibroblast Culture:

Dermal tissue was dissected into <0.5 mm$^3$ fragments and grown in DMEM supplemented with 10% FCS and glutamine and the cells were used for experimentation between passages 0 and 3. They were grown to confluence before splitting and rinsed twice with PBS and counted.

Cells were plated in 60 or 100 mm diameter Falcon culture dishes and grown to 75% confluence. Just prior to irradiation or chemical treatment of cells, the growth medium was removed and the cell monolayer was rinsed twice with phosphate-buffered saline (PBS, 0.14 M NaCl; 2.7 mM KCL; 8.1 mM $Na_2HPO_4$, 1.5 mM $KH_2PO_4$). For UVA irradiation, cells were covered with PBS and irradiated at 25° C. Irradiation periods were on the average from about 13 to 55 minutes maximum. For hydrogen peroxide treatment, cells were covered with PBS containing the appropriate concentration of $H_2O_2$ (0.1-2.4 mM) are treated 30 min at 37° C. in a 5% $CO_2$ incubator.

Survival Analysis:

Dishes of cells (60 mm, ~75% confluent) that had received either hydrogen peroxide or UVA radiation treatments were trypsinized, diluted, and plated at 200-5000 cells per dish (60 mm, three dishes per treatment). The dishes were incubated at 37° C. for 12 to 14 days, after which they were stained with methylene blue and the colonies (>20 cells) were counted with the aid of a dissecting microscope. All experiments were carried out with both the laminar flow hood illumination system and room fluorescent lights extinguished.

Cell Growth Characteristics and Stability:

Cell growth curves were established for fetal and adult human skin fibroblasts. Cells from flasks at 75% confluence were trypsinized and counted. Plates of 1000 cells were established in triplicate and counted at various time points between 5 and 20 days.

Cells (fetal and adult skin fibroblasts) were also frozen under several conditions as cell pellets at −20° C., −80° C. and with liquid nitrogen and also in association with different concentrations of DMSO. The stability of cells was also determined by refrigerating cells either in pellets or associated in a collagen matrix.

Immunohistochemistry:

Fixed tissue sections of 5 μm thickness were used for the immunohistochemistry. All incubations were done in a humidified chamber in the dark unless otherwise specified.

For p63 detection, non-specific binding was blocked by an incubation for 2 hr at 25° C. with a solution of PBS containing 5% fetal calf serum (FCS), 7% normal goat serum (NGS) and 0.1% Triton X 100. Tissue sections were then incubated with p63 specific antibodies (p63[a p53 homolog at 3q27-29] Ab-1, Clone 4A4) at a 1:2000 dilution in PBS containing 5% FCS, 5% NGS and 0.1% Triton X 100 for 30 minutes (Neomarkers, Fremont, Calif., USA). Immediately following this incubation (p53), tissue sections were washed 3 times for 10 minutes each in PBS and the sections treated with biotinylated goat anti-rabbit at 1:2000 in a solution of PBS with 5% FCS, 1% NGS and 0.1% Triton X 100 for 3 hours at 25° C. Tissue sections were washed 4 times for 5 minutes each in PBS and then treated with Vectastain ABC® (Vector, Burlingame, Calif.) as indicated by the company for 3 hours at 25° C. After this incubation, tissue sections were washed 3 times for 10 minutes each in PBS and treated with 0.5 mg/ml 3,3'-diaminobenzidine with 0.32 μl % $H_2O_2$ added just before an incubation of 1-2 minutes. All samples were treated at the same time. The antibody staining for p63 is represented by the brown coloration. The samples were washed for 5 minutes under running water. They were counterstained with Papanicolaou (Harris' Hematoxylin solution), dehydrated and mounted with Merckoglas® (Merck, Switzerland)

Results:

Cell Populations Obtained in Large Quantities:

The skin, like many other tissues, is constantly replenished with new cells produced by stem cells. One of the genes in skin cells that is vital for maintaining epithelial stem cells is p63, which provides an excellent marker for locating these cells in the epidermal layer of skin. It has been shown, at least with a mouse model, that in the absence of p63, regenerative proliferation for limbs, craniofacial and epithelial development is not efficient. (Yang et al., Nature 398: 714-718, 1999). In fetal skin, the epidermis is only 1-2 layers thick at 12-14 weeks of gestation and ~2-4 cell layers thick at about 16 weeks. In all of the layers of skin during development, it is possible to detect strong p63 nuclear marking in all epidermal cells and in developing hair follicles. These cells (stem cells, p63+ epidermal keratinocytes) have gained much attention because of their ability to produce different cell types but little is known how they function and why they are able to constantly proliferate although it seems that p63 plays a role in maintaining the population of epithelial stem cells. The dermal tissue does not contain individual p63+ cells and there is not yet a marker identified that characterized the dermal fibroblasts that are capable of rapid regeneration.

Figure 2A:
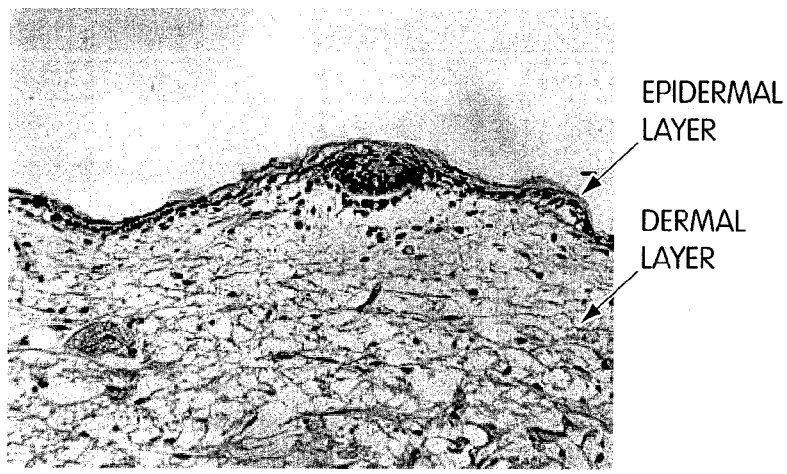
FIG. 2a is a photomicrograph showing the results of immunohistochemistry analysis of fetal skin stained with p63 antibodies showing p63$^+$ epidermal keratinocyte population of cells in culture along with the dermal fibroblast cells (bar is equivalent to 50 μm).
Figure 2B:
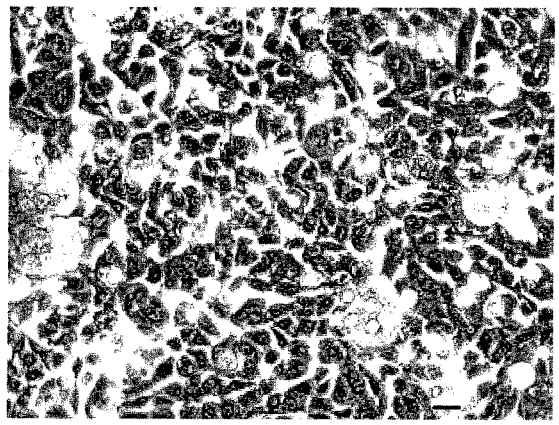
FIG. 2b is a photomicrograph that shows the results of immunohistochemistry analysis of the fetal epithelium layer.
Figure 2C:
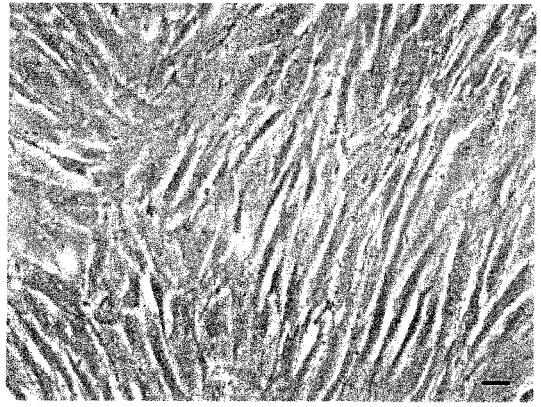
FIG. 2c is a photomicrograph that shows the results immunohistochemistry analysis of the fetal dermal layer.

Both epidermal keratinocytes and dermal fibroblasts were cultured separately from fetal skin. Epidermal cells were all p63+(FIG. 2a) and pure cell cultures were obtained from the epithelium (FIG. 2b) and from the dermal tissue (FIG. 2c). Keratinocytes are much more resistant to oxidative stress when compared to the underlying dermal fibroblasts (Applegate et al., European Journal of Dermatalogy 7:215-219, 1997; Applegate et al., Landmarks in Photobiology pp. 259-263, 1998; and Applegate et al., JID 111:159-163, 1998). As this was also observed for the fetal cells, the fibroblasts from fetal and old skin were used to characterize the differences in resistance to physical and oxidative type stresses.

Figure 3:
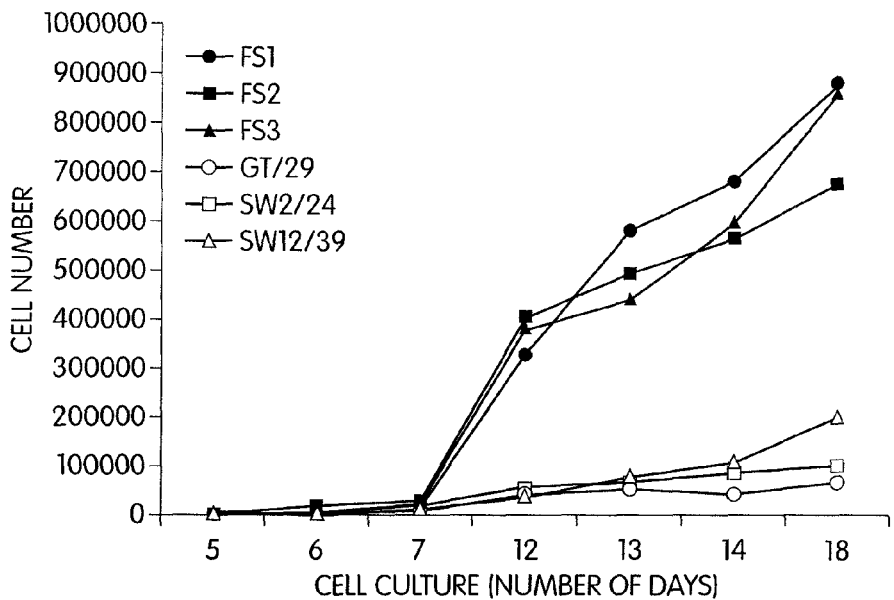
FIG. 3 is a graph showing cell growth of dermal skin fibroblasts (cell number) as a function of time for three individual fetal skin cell lines (closed symbols) and three adult skin cell lines (open symbols) starting with 1000 cells for each sample.
Figure 4:
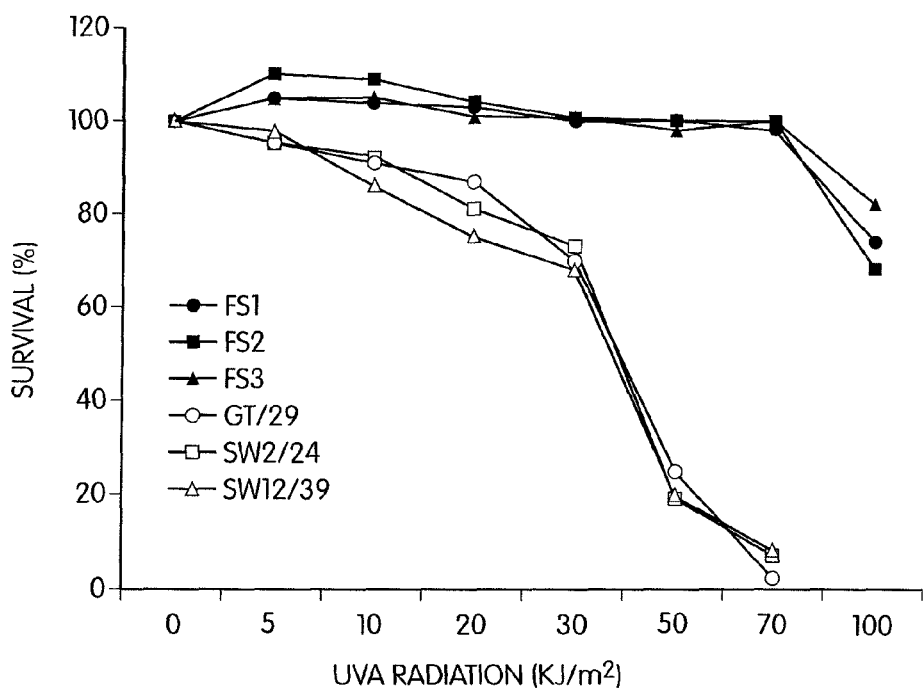
FIG. 4 is a graph showing percentage survival of dermal skin fibroblasts as a function of exposure to UVA radiation for three individual fetal skin cell lines (closed symbols) and three adult skin cell lines (open symbols). Each data point is represented by the average number of clones from three culture plates.

Cell Growth and Stability of Fetal Versus Adult Skin Fibroblasts:

The cell growth of fetal skin fibroblasts has been shown to be much greater than of skin fibroblasts of adult donors. From the first day when fetal skin fragments are placed into culture dishes, one is able to discern fibroblast outgrowth, See FIG. 3, fetal skin fragments (represented by closed circles (FS1), closed squares (FS2) and closed triangles (FS3)) The same is usually observed after 5-6 days for adult skin fragments treated under the same conditions, See FIG. 3, adult skin fragments (represented by open circles (GT/29), open squares (SW2/24) and open triangles (SW12/39)). Once cultures are established, the fetal cells continue to grow at a much faster rate than cells from adults. (See FIG. 3). By simply analyzing the cell number as a function of days in culture when starting with a low number of cells (100 or 1000), there exists a sharp difference at 12 days of culture. This is perhaps due to the difference in cloning efficiency which is approximately 83-91% for fetal cells and 10-22% for adult cells.

In the same manner, fetal cells frozen as simple cell pellets even at −20° C. for up to 3 months are able to show similar outgrowth as when under normal freezing conditions with DMSO in liquid nitrogen. Adult skin fibroblasts (two of the three cell lines) can show a limited amount of cell growth at −80° C. freezing conditions with DMSO as a conserving agent but not at −20° C. Fetal skin fibroblasts were even able to show considerable cell growth following refrigeration of 2 weeks.

Cell Survival of Fetal Versus Adult Skin Fibroblasts Following UVA Radiation:

Neonatal fibroblasts from foreskin tissue are more resistant to oxidative stress. (Applegate et al., JID 102:762-767, 1994). It was of interest to see how cells from different ages of gestation reacted also to oxidative stress and compare their resistance to adult skin cells. Even though there exists a great difference between fetal cells and adult cells regarding their resistance to UVA radiation as the oxidative stress, no differences were seen between ages 12-16 weeks in gestation. By looking at the percentage of survival as a function of UVA radiation dose, there is an extreme resistance marked in the three fetal skin cell lines (represented by closed circles (FS1), closed squares (FS2) and closed triangles (FS3) tested in early passage number when compared to adult skin cell lines (represented by open circles (GT/29), open squares (SW2/24) and open triangles (SW12/39) in the same passage. (See FIG.

4). Even following the highest dose of UVA radiation (taking approximately 50 minutes), only approximately 20% of the fetal cells were killed. In contrast, a dose of 30-50 KJ/m² (a dose that gives a perceptible erythema to human skin) was capable of killing 50% of adult skin cells.

Figure 5:
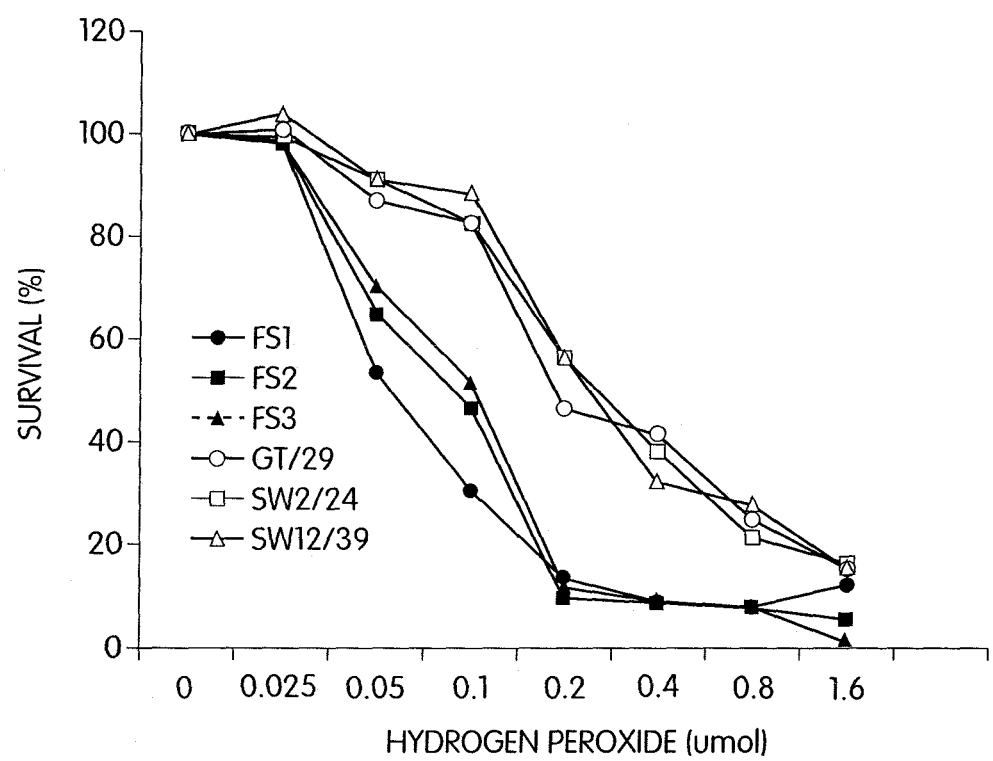
FIG. 5 is a graph showing percentage survival of dermal skin fibroblasts as a function of treatment with hydrogen peroxide for three individual fetal skin cell lines (closed symbols) and three adult skin cell lines (open symbols). Each data point is represented by the average number of clones from three culture plates.

Cell Survival of Fetal Versus Adult Skin Fibroblasts Following $H_2O_2$ Treatment:

The inactivation curves for the adult skin fibroblast are biphasic in nature, which is characteristic of the use of hydrogen peroxide as the oxidizing agent. However, this is not seen for the fetal skin cells (represented by close circles (FS1), closed squares (FS2) and closed triangles (FS3) and there is a gradual decrease in cell survival with an increasing concentration of hydrogen peroxide. The fetal skin cells are 1.5 times more resistant to this type of oxidizing stress when compared to adult skin cells (represented by open circles (GT/29), open squares (SW2/24) and open triangles (SW12/39) under the same culture conditions and passages. (See FIG. 5).

Fetal cells have proven to be resistant to physical and oxidative type stresses which seem to afford a great stability to these cells. It is unknown why fetal cells are much more resistant to oxidative stress. Without being limited by any particular mechanism, it is possible that they may be more efficient in scavenging potential damaging free radical intermediates or perhaps they are more efficient in processing and repairing oxidative damage to critical cellular targets. Interestingly, in preliminary studies looking at proteins by 2-D gel analysis in fetal cells in low and high passages, several proteins have been identified that change dramatically and that are implicated in oxidative stress functions.

Example 4

Veterinarian Applications with Three-Dimensional Cutaneous Tissue Allograft Constructs The horse, because of its utilization in sport, is particularly exposed to cutaneous injury. Cutaneous wound healing in horses, is particularly long and difficult to treat, and has several interesting aspects. Taking into account the loss of substance and the parallel tissue damage, traumatic wounds can rarely be sutured. In addition, the horse is predisposed to excessive tissue granulation, which inhibits tissue repair processes. Specifically, there is an inhibition of epithelial formation and a promotion of cheloid formation. This tendency for excessive tissue granulation can have severe consequences for aesthetic quality and can lead to long periods of immobilization for the animal. These factors can contribute to a diminished financial value for the animal and for its utilization. Consequently, for a racehorse that has been injured, it is not rare that there is a need for 4 to 6 months of immobilization, which in turn, leads to a direct competitive loss. Thus, there is a need for a tissue repair product that is capable of stimulating epidermal renewal at wound sites in equines, in very short periods of time.

A collagen sponge that is made from horse tendon was seeded with fetal horse cells (undifferentiated fibroblasts/keratinocytes) and cultured in tissue culture medium in the presence of horse serum. The process of producing the cutaneous allograft construct was performed as disclosed in Example 2, however fetal horse cells are used instead of fetal human cells. Two skin defects were tested using the three-dimensional cutaneous tissue allograft construct prepared according to this method.

Figure 6A:
FIG. 6a is a photograph representing a deep abscess on the jaw of a horse with elimination of a tooth-abscess penetrating from the inside of the mouth to the outside surface creating ulceration.
Figure 6B:
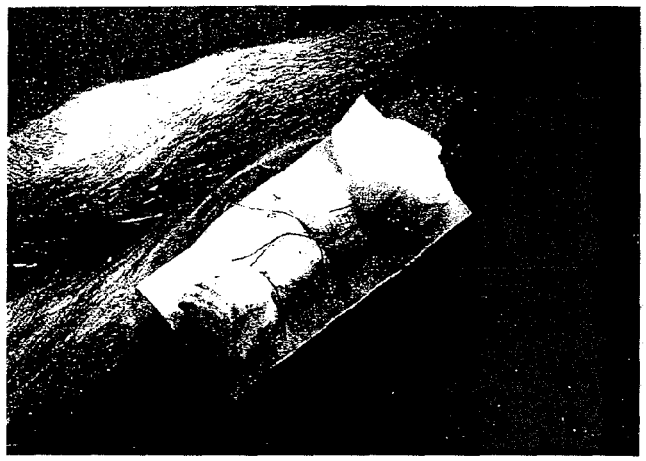
FIG. 6b is a photograph representing the three-dimensional cutaneous tissue allograft positioned at the site of the wound on the horse.
Figure 6C:
FIG. 6c is a photograph representing the wound area on the horse, one week after placement of the three-dimensional cutaneous tissue allograft. This figure shows complete closing and elimination of the abscess (ulcer).

Patient 1 was an equine having a deep abscess of the jaw. The tooth-abscess penetrated from the inside of the mouth to the outside surface, creating an ulcer. The horse was prepped for surgery, and the wound was cleaned with NaCl. The allograft construct was prepared and positioned at the abscess as shown in FIG. 6a. The allograft construct was then covered with a bandage and stitched into place as shown in FIG. 6b. One week after the initial surgery, there was complete closing and elimination of the abscess. (See FIG. 6c).

Figure 7A:
FIG. 7a is a photograph representing a deep wound on the knee of a horse which penetrates through skin and muscle to the bone.
Figure 7B:
FIG. 7b is a photograph representing a bi-layered three-dimensional allograft within muscle (internal) which contains muscle fetal cells, and skin (external), which contains fetal skin cells on a horse.
Figure 7C:
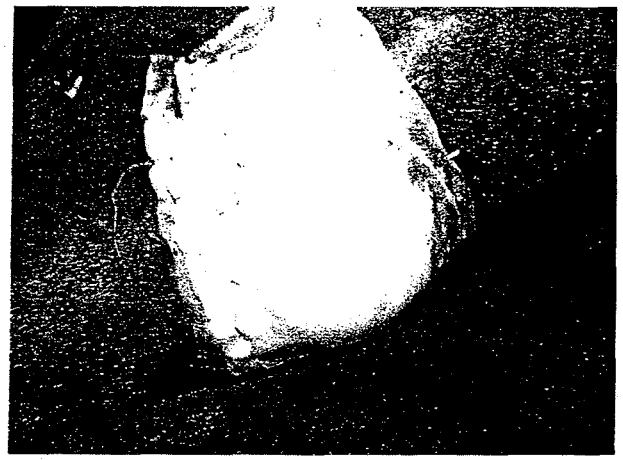
FIG. 7c is a photograph representing the bi-layered, three-dimensional allograft positioned at the site of the wound on the horse.
Figure 7D:
FIG. 7d is a photograph representing the wound area two days after placement of the bi-layered, three-dimensional allograft on the horse. This figure shows that only surface involvement remains.

Patient 2 was an equine having a deep wound on the knee that went through the skin, muscle and to the bone. (See FIG. 7a). The horse was prepped for surgery and the wound cleaned. A bi-layer graft was used to treat this wound. One layer covered the muscle (and included undifferentiated fetal muscle cells) and one layer covered the skin (and included undifferentiated fetal skin cells). The allograft construct was positioned at the site of the wound (FIG. 7b) and was then covered with bandages and stapled in place (FIG. 7c). Two days after surgery, the wound appeared to be healing in both the bone and muscle layers (FIG. 7d) with only surface involvement remaining.

Example 5

Human Applications with Three-Dimensional Cutaneous Tissue Allograft Constructs

Cell lines were created using the techniques outlined in Example 2, supra. Approximately three to five days prior to grafting date on the patient, 9×12 cm sheets of equine collagen were seeded with 1×10⁵ cells/cm² (cells used from passages 0 to 3) by making small incisions into the matrix with sterile, small-bored pipette tips. Medium was then added to the culture plate one hour later and changed every two days. The three-dimensional cutaneous tissue allograft produced contained undifferentiated epidermal keratinocytes (10-13.5%) and undifferentiated dermal fibroblasts (90-86.5%).

Patients treated in this study were selected on the basis of a history of having chronic leg ulcers which would not close using other traditional therapies (contention bandaging, autografts, etc.). Assessment of each patient was done by Doppler and absence of arteriopathology. The chronic ulcers were then cleaned with physiological saline and mechanical preparation with a curette. The fetal cell allograft constructs were applied to cover the entire wound surface followed by a layer of Vaseline gauze and standard gauze bandages. Allograft constructs were applied one time a week followed by 4 days to bandage change. Bandages were then changed every two days.

A total of 11 patients were treated with fetal cell therapy concerning 21 ulcers. Of these, 15 ulcers closed completely, 3 exhibited with significant amelioration in size (but not complete closure) and 3 were lost to follow-up because the patients estimated that there was a substantial improvement. The details of 2 patients are presented herein. Table 3 summarizes all patients treated with fetal cell therapy.

Figure 8:
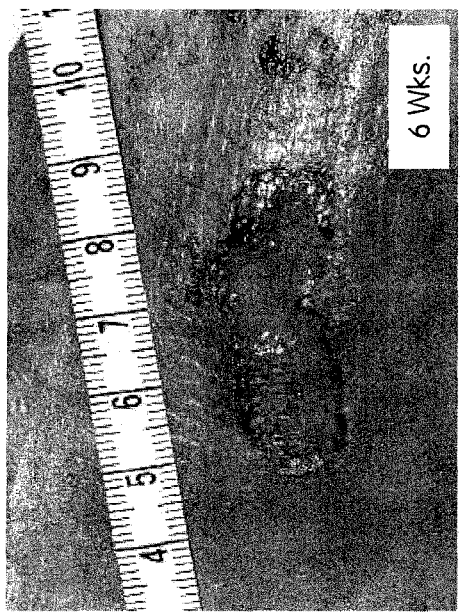
FIG. 8 is a photograph representing a human patient with polio-arthritis having a resistant mixed ulcer at the ankle articulation.
Figure 8:
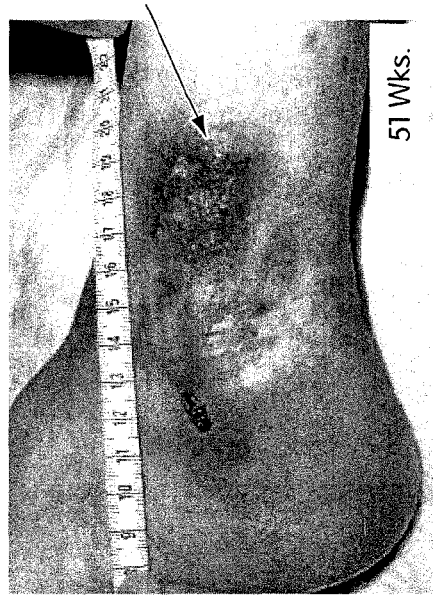
Figure 8:
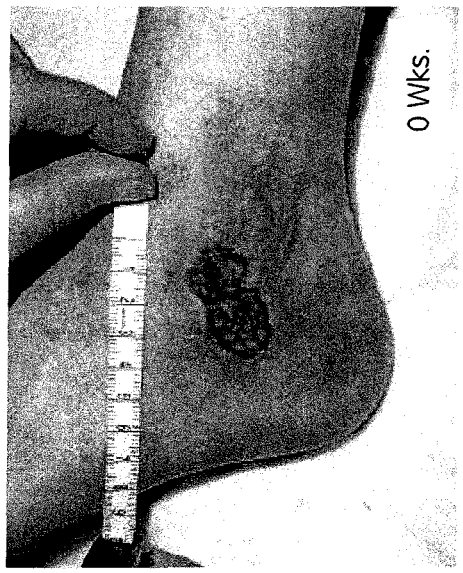
Figure 8:
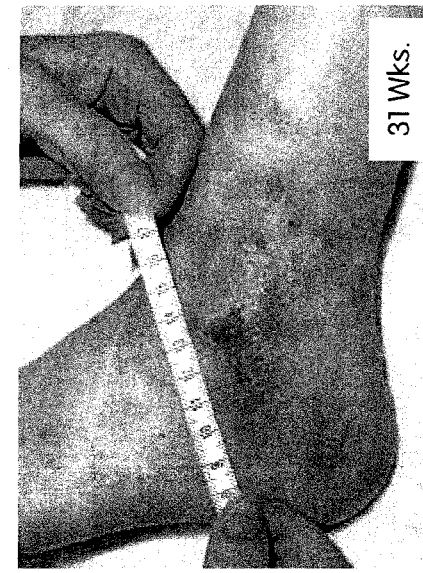

Patient 1 was a female having rheumatoid arthritis. A resistant arterial and venous ulcer, measuring 2×4.5 cm, existed at the ankle articulation which had been present for 18 months. Two graft applications with Apligraft® were not successful. The patient presented with a history of multiple allergies and severe pain in and around the ulcer lesion. After much difficulty in finding a sufficient cover (due to an allergy to all types of bandages) and several months of non-compliance for wound preparation, the patient finally agreed to the elimination of the fibrin barrier in the wound so that a subsequent application of fetal grafts could take place effectively. The patient was treated with a total of 31 allograft constructs. Immediately after preparation of the wound bed, there was a decrease in pain and continual reduction in size of the ulcer. A small change in the type of gauze utilized at the end of treatment (due to a rupture of stock in the hospital) was sufficient to irritate surrounding skin. These results are presented in FIG. 8.

Figure 9:
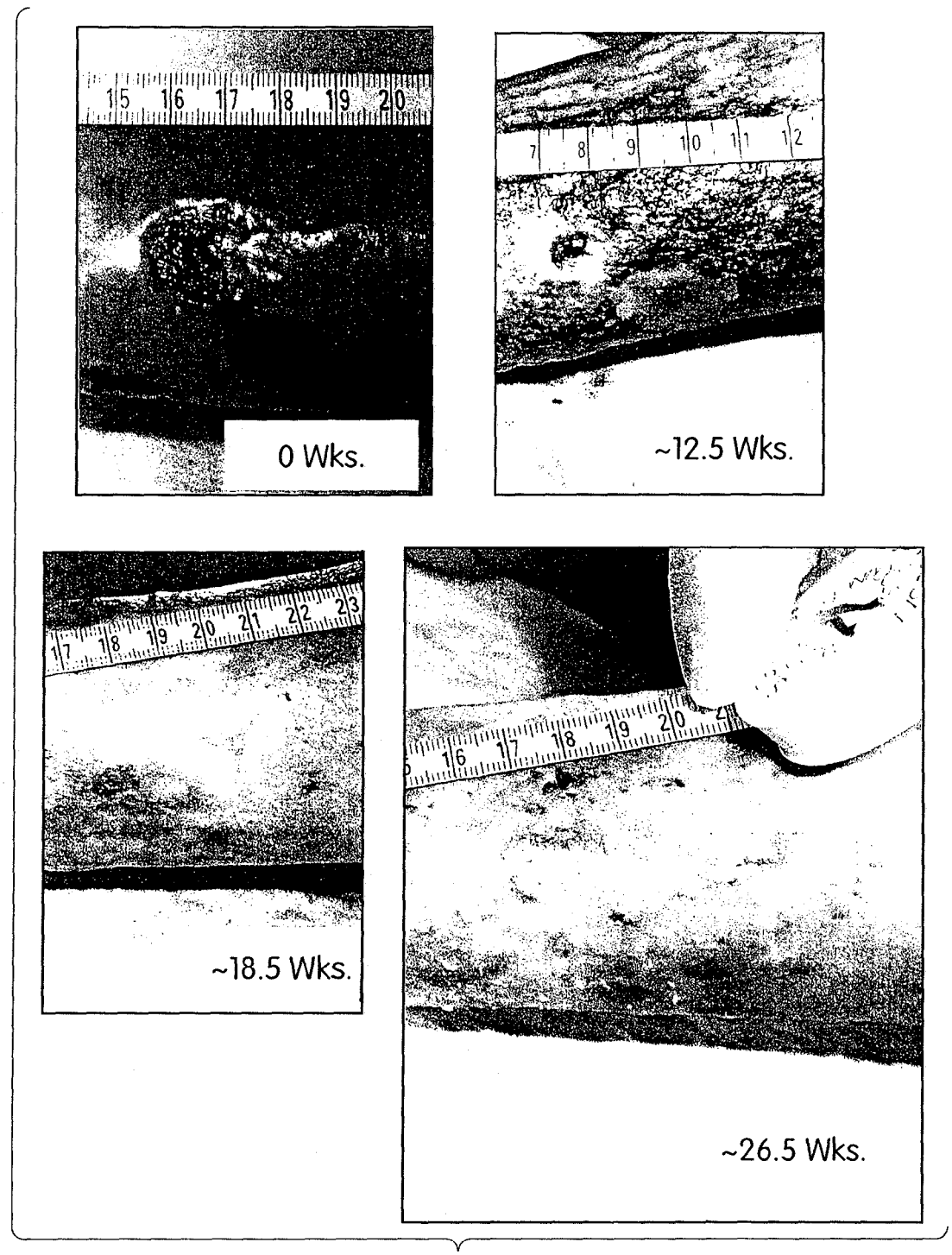
FIG. 9 is a photograph representing a human patient having four ulcers on the lower left leg, present for two years. After treatment with the three-dimensional cutaneous tissue allograft of the invention, complete closure of 2 of the ulcers is seen within approximately 7 months of treatment.

Patient 2 was a female with four ulcers on the lower left leg. The ulcers measured 4×2.5 cm (10 allograft constructs were received in total); 3×2 cm (12 allograft constructs were received in total); 3×2 cm (24 allograft constructs were received in total); and 2.5×2 cm (24 allograft constructs were received in total). The ulcers had been present for two years, and the patient was anemic, dehydrated and very thin. Previous treatment with 4 autografts and 4 Apligraft® administrations were unsuccessful. Immediate improvement of leg congestion and pain was observed following one treatment with the fetal cell therapy of the invention. Progressive and rapid improvement was seen in two of the ulcers, which closed in a period of several weeks. The two remaining ulcers also showed amelioration, but complete closure was not possible. Autografts were subsequently tried on the two remaining ulcers without success. These results are presented in FIG. 9.

-continued

| | |
|---|---|
| Fragrance - 0.5% | PPG-25-Laureth-25 - 0.5% |
| PEG-5 Pentaerythrityl Ether - 0.4% | Ricinoleth-40 - 0.32% |
| Hydroxyethylcellulose - 0.3% | Glucose - 0.2% |
| Sodium Chloride - 0.2% | Methylparaben - 0.14% |
| Simethicone - <0.1% | Ascorbyl Palmitate - 0.08% |
| Tocopheryl Acetate - 0.08% | Imidazolidinyl Urea - 0.08% |
| Propylparaben - 0.05% | Potassium Chloride - 0.05% |
| Magnesium Chloride - 0.04% | |

Cell lines were created using the techniques outlined in Example 2 above. Cells from passages 5-10 were prepared for a final concentration of $5.3 \times 10^3$ cells/ml and fetal proteins were stabilized by gradual freezing at 1 degree per hour to a final temperature of −80° C. The cream composition, an oil-in-water mixture, was heated gradually for the incorporation of the fetal proteins.

Patient 1 was a female diagnosed with Atrophie blanche. The patient had a persistent leg ulcer. After two weeks of treatment

TABLE 3

Evolution of Patients Treated with Fetal Cell Therapy

| Sex | Ulcer Type | Number of Allograft Constructs | Fetal Cell Therapy Results | Other Treatment Results |
|---|---|---|---|---|
| F | | 19 | Progressive evolution, but not closed. | Hospitalized for autograft with no success, followed by 3 weeks Unna's Boot. Still in treatment |
| F | Venous, Right Leg | | | |
| | 1. 13 × 4 cm-Deep | 17 | Ulcer healed completely. | |
| | 2. 4 × 2 cm | 5 | Ulcer healed completely. | |
| F | Venous, Left Leg 5 × 4 cm-Deep | 19 | Ulcer healed completely. | |
| F | Atrophie Blanche Deep | 14 | Progressive evolution, but not closed. | Hospitalized for autograft. Miraculously closed with preparatory VAC |
| F | Venous, Left Leg | | | Hospitalized for autograft with no success, still in treatment. |
| | 1. 4 × 2.5 cm | 10 | Ulcer healed completely. | |
| | 2. 3 × 2 cm | 12 | Ulcer healed completely. | |
| | 3. 3 × 2 cm | 24 | Progressive evolution, but not closed. | |
| | 4. 2.5 × 2 cm | 24 | Progressive evolution, but not closed. | |
| F | Poly-arthritis LL 2 × 4.5 cm | 31 | Ulcer healed completely. | |
| F | Venous, Right Leg 4 × 2 cm | 7 | Ulcer healed completely. | |
| M | | 4 | Good progressive evolution. Patient stopped in-clinic treatments. | |
| F | Atrophie Blanche | 3 | Ulcer healed completely. | |
| F | Arterial, Left Leg | | | |
| | 1. 4 × 2 cm | 3 | Progressive evolution, but not closed. | |
| | 2. 2 × 2 cm | 3 | Progressive evolution, but not closed. | |

Example 6

Human Applications with Cream Composition

Figure 11:
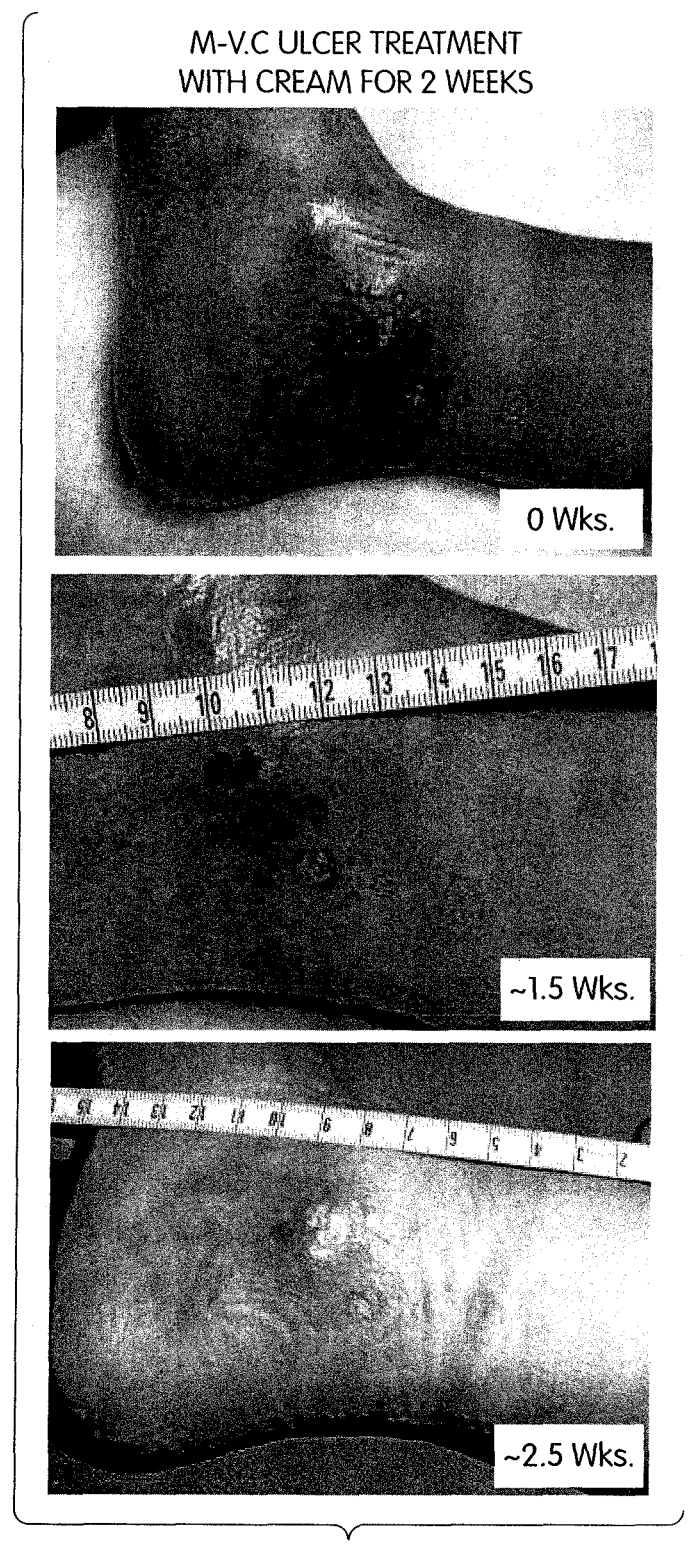
FIG. 11 is a photograph representing a human patient having an ulcer at the ankle. After approximately two weeks of treatment with the composition of the invention, results indicate closure of the ulcer.

A topical composition containing undifferentiated fetal skin cells and a carrier was prepared in the form of a cream. This composition contained the following ingredients:

| | |
|---|---|
| Purified Water - 68.51% | Hydrogenated Vegetable Oil - 10.0% |
| Glycerin - 5.0% | Propylene Glycol - 4.9% |
| Cetearyl Octanoate - 2.0% | Cetearyl Alcohol - 1.35% |
| Hydrolyzed Glycosaminoglycans - 0.7% | PEG-8 C12-18 Ester - 0.7% |
| Cetyl Alcohol - 0.7% | Cetyl Palmitate - 0.7% |
| Hydrolyzed Actin - 0.7% | Hydrolyzed Fibronectin - 0.6% |
| Glyceryl Stearate - 0.6% | Hydrolyzed Keratin - 0.5% | with the cream composition of the invention, the ulcer appeared to be completely closed, as shown in FIG. 11.

Example 7

Human Applications with Combination Therapy—Three-Dimensional Cutaneous Tissue Allograft and Cream Composition Patient 1 was a female diagnosed with Atrophie blanche on both lower leg regions. The ulcer on the right lower leg had been present for 20 months and was extremely fibrous in nature. As all of the lower leg skin was atrophic, the three-dimensional cutaneous tissue allograft construct was applied in conjunction with the cream composition of the invention to cover the entire region around the ulcer.

Figure 12:
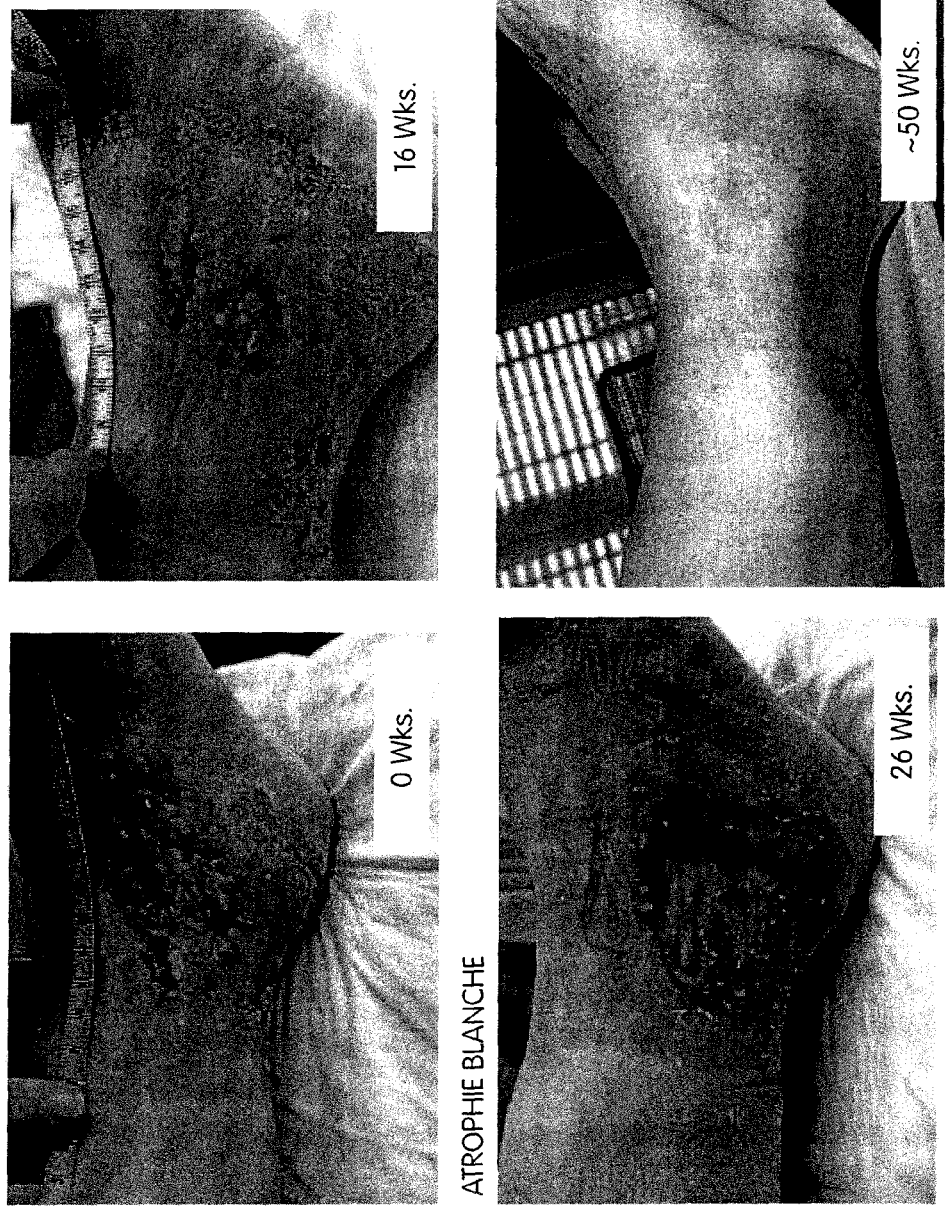
FIG. 12 is a photograph representing a human patient with Atrophie blanche on both lower leg regions. A three-dimensional cutaneous tissue allograft and composition, in the form of a cream, were applied. Results indicate closure of the ulcers.

Following this fetal cell therapy, the congestion and itching was eliminated immediately and the original ulcer closed gradually. Even though the ulcer of origin closed, a new parallel ulceration formed because of the instability of the skin. For better wound preparation, this patient had vacuum assisted closure (VAC) applied for one week with the intention of applying an autograft. Surprisingly, the ulcer and associated minor ulcerations were closed following VAC. Previously, several hundred patients had been treated with only VAC for one week, and no wound closure was observed. At the one year follow-up, the patient's Atrophie blanche was stable and no new ulceration was observed. These results are presented in FIG. 12.

Figure 10:
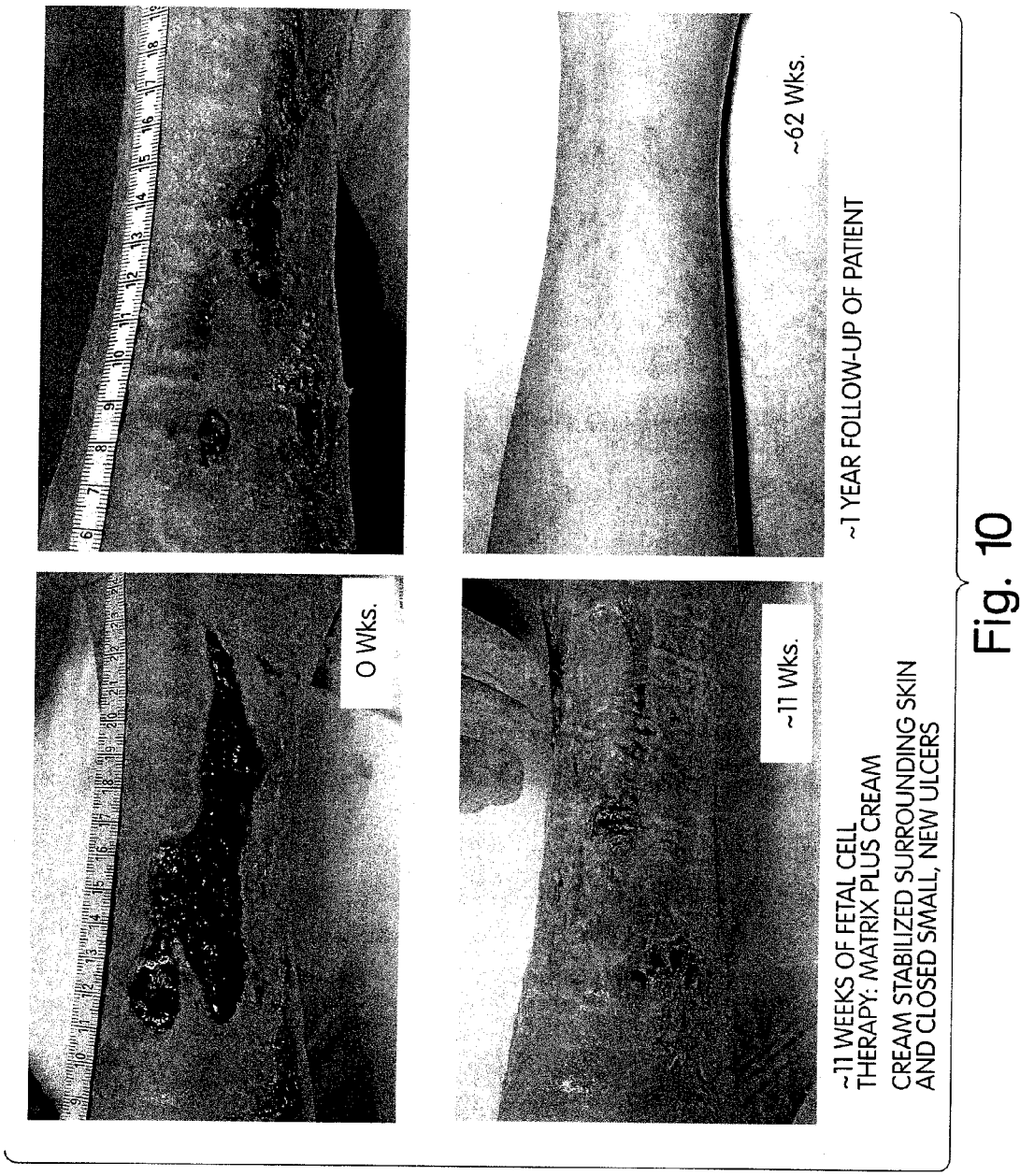
FIG. 10 is a photograph representing a human patient with a history of the same leg ulcer for 10 years. Immediately following the first three-dimensional cutaneous tissue allograft, congestion, pain and fibrin production elimination was evident. At the one year follow-up, the skin is still atrophic, but there is no presence of scar tissue.

Patient 2 was a female with a history of the same leg ulcer for 10 years. Previous autografts and different bandaging therapies were unsuccessful. Immediately following the application of the first fetal cell allograft construct and cream, elimination of the congestion, pain, and fibrin production was evident. Rapid, progressive closure was observed for this large, deep and painful ulcer. The cream stabilized the peripheral skin and prevented new ulcers. At the one year follow-up, the skin was still atrophic but there was no presence of scar tissue. These results are presented in FIG. 10.

Other Embodiments

From the foregoing detailed description of the specific embodiments of the invention, it should be apparent that unique methods and compositions have been described. Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims.

We claim:

1. A collagen sheet comprising undifferentiated human fetal skin cells;
   wherein the undifferentiated human fetal skin cells can differentiate into human dermal fibroblasts, for treating a skin condition, disorder or disease in a subject in need thereof without scar formation upon topical administration;
   wherein said undifferentiated human fetal skin cells are from a human donor tissue of 12-16 weeks gestation;
   wherein said undifferentiated human fetal skin cells are seeded into the collagen sheet in the form of a three-dimensional tissue construct; and
   wherein said collagen sheet can be applied to the subject in any orientation.

2. The composition of claim 1, wherein the collagen sheet is a human collagen.

3. The composition of claim 1, wherein the collagen sheet is a horse collagen.

4. A composition comprising a carrier and undifferentiated human fetal skin cells in the form of a cream formulation for a topical administration for treating a skin condition, disorder or disease in a subject in need thereof without scar formation upon topical administration;
   wherein the undifferentiated human fetal skin cells can differentiate into human dermal fibroblasts;
   wherein said undifferentiated human fetal skin cells are from a human donor tissue of 12-16 weeks gestation; and
   wherein the cream formulation comprises 68.51% (by weight) water, 10.0% (by weight) hydrogenated vegetable oil, 5.0% (by weight) glycerin, 4.9% (by weight) propylene glycol, 2.0% (by weight) cetearyl octanoate, 1.35% (by weight) cetearyl alcohol, 0.7% (by weight) hydrolyzed glycosaminoglycans, 0.7% (by weight) PEG-8 C12-18 ester, 0.7% (by weight) cetyl alcohol, 0.7% (by weight) cetyl palmitate, 0.7% (by weight) hydrolyzed actin, 0.6% (by weight) hydrolyzed fibronectin, 0.6% (by weight) glyceryl stearate, 0.5% (by weight) hydrolyzed keratin, 0.5% (by weight) fragrance, 0.5% (by weight) PPG-25-Laureth-25, 0.4% (by weight) PEG-5 pentaerythrityl ether, 0.32% (by weight) Ricinoleth-40, 0.3% (by weight) hydroxyethylcellulose, 0.2% (by weight) glucose, 0.2% (by weight) sodium chloride, 0.14% (by weight) methylparaben, less than 0.1% (by weight) simethicone, 0.08% (by weight) ascorbyl palmitate, 0.08% (by weight) tocopheryl acetate, 0.08% (by weight) imidazolidinyl urea, 0.05% (by weight) propylparaben, 0.05% (by weight) potassium chloride, and 0.04% (by weight) magnesium chloride.

5. A method for treating a skin condition, disorder or disease in a subject suffering from said skin condition, disorder or disease, comprising cutaneously administering a therapeutically effective amount of the composition of claim 3 to an affected area of the subject's skin.

6. The method of claim 5, wherein the skin condition, disorder or disease is selected from the group consisting of wounds, skin defects and skin conditions.

7. The method of claim 6, wherein the wound is an acute wound.

8. The method of claim 7, wherein the acute wound is selected from the group consisting of minor cuts, burns, dry skin, skin tears, skin lacerations, surgical wounds, accidental trauma and hypertrophic scars.

9. The method of claim 6, wherein the wound is a chronic wound.

10. The method of claim 9, wherein the chronic wound is selected from the group consisting of venous ulcers, pressure ulcers, diabetic ulcers, arterial ulcers, burns, and peri-ulcers.

11. The method of claim 6, wherein the skin defect is selected from the group consisting of eczema, psoriases, radiodermatitis, skin cancer, urticaria, livedoid vasculitis, severe dryness, Atrophie blanche, vestibulitis, blemishes, age spots, scars, bruises, birthmarks, tattoos, hyperpigmentation, atrophic dermatitis, severely creviced and chapped hands, and keloids.

12. The method of claim 6, wherein the skin condition is an inflammatory skin condition.

13. The method of claim 6, wherein the skin condition is selected from the group consisting of blemishes, age spots, scars, burns, bruises, birthmarks, tattoos, hyperpigmentation, atopic dermatitis, peri-ulcers, eczema, radiodermatitis, ulcers, urticaria, severe dryness, Atrophie blanche and vestibulitis.

14. The method of claim 13, wherein the skin condition is a peri-ulcer.

15. The method of claim 13, wherein the skin condition is Atrophie blanche.

16. The method of claim 13, wherein the skin condition is hyperpigmentation.

17. The method of claim 13, wherein the skin condition is vestibulitis.

18. The method of claim 5, wherein the subject is human.

19. The method of claim 5, wherein the subject is a horse.

* * * * *